US011512294B2

(12) United States Patent
Nicol et al.

(10) Patent No.: US 11,512,294 B2
(45) Date of Patent: Nov. 29, 2022

(54) CYCLIC GMP-CHELATING PEPTIDES FOR SUBCELLULAR TARGETING

(71) Applicants: SORBONNE UNIVERSITÉ, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(72) Inventors: Xavier Nicol, Chatou (FR); Oriol Ros Torres, Paris (FR)

(73) Assignees: SORBAOONE UNIVERSITE, Paris (FR); CENTRE NATIONAL DE LA RECHARCHE SCIENTIFIQUE, Paris (FR); INSTITUT NATIONAL DE LA SANTE ET LA RECHERCHE MEDICALE (INSERM), Paris (FR)

( * ) Notice: Subject to any disclaimer, the term of this patent is extended or adjusted under 35 U.S.C. 154(b) by 121 days.

(21) Appl. No.: 16/759,703

(22) PCT Filed: Nov. 2, 2018

(86) PCT No.: PCT/EP2018/080043
§ 371 (c)(1),
(2) Date: Apr. 27, 2020

(87) PCT Pub. No.: WO2019/086622
PCT Pub. Date: May 9, 2019

(65) Prior Publication Data
US 2020/0299653 A1 Sep. 24, 2020

(30) Foreign Application Priority Data
Nov. 2, 2017 (EP) .................................... 17306511

(51) Int. Cl.
*C12N 9/12* (2006.01)
*A61K 48/00* (2006.01)
*C07K 14/00* (2006.01)
*C12N 15/85* (2006.01)
*C12N 15/87* (2006.01)
*A61K 38/00* (2006.01)

(52) U.S. Cl.
CPC ............ *C12N 9/12* (2013.01); *A61K 48/0075* (2013.01); *C07K 14/00* (2013.01); *C12N 15/85* (2013.01); *C12N 15/87* (2013.01); *C12Y 207/11012* (2013.01); *A61K 38/00* (2013.01); *C07K 2319/60* (2013.01)

(58) Field of Classification Search
None
See application file for complete search history.

(56) References Cited

PUBLICATIONS

Dostmann, W.R.G., et al., "The Catalytic Domain of the cGMP-Dependent Protein Kinase Iα Modulates the cGMP-Binding Characteristics of Its Regulatory Domain," FEBS Letters 398(2-3):206-210, 1996.
International Search Report dated Dec. 12, 2018, issued in corresponding International Application No. PCT/EP2018/080043, filed Nov. 2, 2018, 4 pages.
Viswanathan, V., et al., "Regulation of Spine Morphology By Cyclic GMP-Dependent Protein Kinase Type II," Program No. 144.19, Dendritic Growth & Branching II, Database Biosis, Biosciences Information Service, Philadelphia, PA,2003, Online.
Written Opinion dated Dec. 12, 2018, issued in corresponding International Application No. PCT/EP2018/080043, filed Nov. 2, 2018, 6 pages.
International Preliminary Report on Patentability dated May 5, 2020, issued in corresponding International Patent Application No. PCT/EP2018/080043, filed Nov. 2, 2018, 7 pages.

*Primary Examiner* — Anand U Desai
(74) *Attorney, Agent, or Firm* — Christensen O'Connor Johnson Kindness PLLC

(57) ABSTRACT

The disclosure pertains to the field of molecular means capable of binding to, and preferably of chelating, cGMP, appropriate for use in vitro or in vivo and preferably capable of targeting specific cellular compartments. The polypeptides of the disclosure comprise a chimeric construction derived from the N terminus part of PKG-Iα and PKG-Iβ, and the two cGMP binding sites of the wild type PKG.

11 Claims, 8 Drawing Sheets
Specification includes a Sequence Listing.

CYCLIC GMP-CHELATING PEPTIDES FOR SUBCELLULAR TARGETING

The invention pertains to the field of molecular means capable of binding to, and preferably of chelating, cGMP, appropriate for use in vitro or in vivo and preferably capable of targeting specific cellular compartments.

cGMP is a second messenger involved in a wide range of signaling pathways and cellular processes including neurotransmission, calcium homeostasis, phototransduction, lipid metabolism and cation channel activity. The diversity of these processes suggest that cGMP signals are tightly controlled in space and time to achieve specific modulation of its downstream pathways. However, manipulating cGMP is mostly achieved using pharmacological approaches either altering the synthesis or degradation of this cyclic nucleotide, or manipulating downstream signaling pathways. This techniques lacks both cellular and subcellular specificity. There is currently no tools capable of binding specifically cGMP and which may be used to altering physiological variations of this second messenger with cellular and subcellular specificity in vitro and in vivo. Recently, optogenetic strategies have emerged to impose acute and extrinsic modulation of cGMP and investigate the dynamics of cGMP signaling. However, they are difficult to use in vivo or for chronic manipulations and are not able to modify endogenous cGMP signals.

The proteins from the cGMP-dependent Protein Kinase (PKG) family are able to bind cGMP, and their cGMP binding sites have been identified.

The proteins of the PKG family are serine/threonine kinases present in a variety of eukaryotes ranging from the unicellular organism Paramecium to humans. Two PKG genes, coding for PKG type I (PKG-I) and type II (PKG-II), have been identified in mammals. The N-terminus of PKG-I is encoded by two alternatively spliced exons that specify for the PKG-I and PKG-I$\beta$ isoforms. PKG-I$\beta$ is activated at about 10-fold higher cGMP concentrations than PKG-I. The PKG-I and PKG-II are homodimers of two identical subunits (about 75 kDa and about 85 kDa, respectively) and share common structural features.

Each subunit is composed of three functional domains:
- an N-terminal domain that mediates homodimerization, suppression of the kinase activity in the absence of cGMP, and interactions with other proteins including protein substrates;
- a regulatory domain that contains two non-identical cGMP-binding sites;
- a kinase domain that catalyzes the phosphate transfer from ATP to the hydroxyl group of a serine/threonine side chain of the target protein In humans, two isoforms of PKG-I have been described: PKG-I and PKG-I$\beta$. The regulatory domain and kinase domain are identical in all PKG-I isoforms, but their N-terminal domains differ.

It is difficult to envision how cGMP chelators could be derived from these proteins. On the one hand, PKG catalytic activity is likely to induce unwanted side effects both when used in vitro as biological tools or when used in a therapeutic treatment, thereby preventing the use of the whole protein. On the other hand, Dotsmann et al. (*FEBS Lett.;* 2; 398(2-3):206-10, 1996) have shown, using deletion mutants of PKG-I, that the deletion of the catalytic domain has a deleterious effect on their affinity constant to cGMP, thus precluding the use of catalytic-deficient proteins derived from the PKG family.

There is thus a need for improved means to manipulate cGMP signaling, and in particular intracellular cGMP concentration.

The inventors have designed chimeric polypeptides derived from the isoforms PKG-I and PKG-I$\beta$, devoid of any catalytic domain. The polypeptides of the invention comprise a chimeric construction derived from the N terminus part of PKG-I and PKG-I$\beta$, and the two cGMP binding sites of the wild type PKG.

Surprisingly, despite the deletion of the catalytic domain, which had been shown to affect PKG-I affinity constant, the PKG-I/PKG-I$\beta$-based chimeric polypeptide of the invention is able to efficiently bind and sequester cGMP. As shown in the experimental part, the polypeptides of the invention are capable of sequestering cGMP after nitric oxide induction, in presence of the FRET sensor $^ThPDE5^{VV}$, thus suggesting its high affinity for cGMP. The polypeptide of the invention can easily be further functionalized using simple molecular tools, for instance by addition of fluorescent peptides. The polypeptide of the invention can therefore be utilized in a wide variety of applications, either in vitro and in vivo, for instance to prevent the activation of cGMP-dependent cellular processes. These properties render the polypeptide of the invention particularly useful for the prevention or treatment of pathologies associated with intracellular cGMP signaling dysfunction.

The invention pertains to a polypeptide comprising:
- a chimeric peptide derived from the sequence SEQ ID NO: 1 and from the sequence SEQ ID NO: 2;
- a cGMP binding domain comprising or consisting of the sequence SEQ ID NO: 6; and,
- wherein said polypeptide is devoid of any catalytic domain, and its functional variants.

The polypeptide of the invention is preferably an isolated, recombinant or synthetic polypeptide.

The sequence SEQ ID NO: 1 corresponds to residues 1 to 89 of bovine PKG-I, which is identical to residues 1 to 89 of human PKG-I. The sequence SEQ ID NO: 2 corresponds to residues 1 to 104 of bovine PKG-I$\beta$, which is identical to residues 1 to 104 of bovine PKG-I$\beta$.

In the context of the invention, the terms 'chimeric peptide derived from the sequence SEQ ID NO: 1 and from the sequence SEQ ID NO: 2_ refer to a peptide comprising or consisting of at least a sequence corresponding to SEQ ID NO: 1 or a fragment thereof, and of at least a sequence corresponding to SEQ ID NO: 2 or a fragment thereof.

The inventors have in particular identified that the following chimeric peptides derived from the sequence SEQ ID NO: 1 and from the sequence SEQ ID NO: 2 are of particular interest when used in the polypeptide:
- the peptide of sequence SEQ ID NO: 3, which corresponds to residues 1-78 of SEQ ID NO: 1, fused to residues 94 to 104 of SEQ ID NO: 2;
- the peptide of sequence SEQ ID NO: 4, which corresponds to residues 1-65 of SEQ ID NO: 2, fused to residues 51-78 of SEQ ID NO: 1, fused to residues 94 to 104 of SEQ ID NO: 2; and,
- the peptide of sequence SEQ ID NO: 5 which corresponds to residues 1-50 of SEQ ID NO: 1, fused to residues 66-83 of SEQ ID NO: 2, fused to residues 69-78 of SEQ ID NO: 1, fused to residues 94 to 104 of SEQ ID NO: 2.

Advantageously, in the polypeptide of the invention, the chimeric peptide consists of or comprises the sequence SEQ ID NO: 3, 4 or 5, preferably the sequence SEQ ID NO: 3

Preferably, the chimeric peptide and the cGMP binding domain form a contiguous sequence, yet preferably the C-terminal end of the chimeric peptide is fused to the N-terminal end of the cGMP binding domain.

According to the invention, the cGMP binding domain comprises or consists of the sequence SEQ ID NO: 6. For the sake of clarity, the sequence SEQ ID NO: 6 corresponds to the consensus sequence for the minimal binding sequence of PKG-I and PKG-II, both of which are known to have the capacity for binding specifically cGMP.

Preferably, the cGMP binding domain comprises or consists of the sequence SEQ ID NO: 7 or the sequence SEQ ID NO: 8. For the sake of clarity, sequence SEQ ID NO: 7 and sequence SEQ ID NO: 8 correspond respectively to the minimal binding sequence of PKG-I and the minimal binding sequence of PKG-II.

Yet preferably, the cGMP binding domain comprises or consists of the sequence SEQ ID NO: 9 or the sequence SEQ ID NO: 10. For the sake of clarity, sequence SEQ ID NO: 9 and sequence SEQ ID NO: 10 correspond respectively to the cGMP binding sequence of human PKG-I and the cGMP binding sequence of bovine PKG-I.

In the context of the invention, the terms 'devoid of any catalytic domain_ should be construed as indicating that the polypeptide of the invention does not contain any of the catalytic domains of either PKG-I or PKG-I$\beta$, nor any other catalytic domain derived therefrom.

In the context of the invention, the terms 'catalytic domain of PKG-I _ refer to the sequence SEQ ID NO: 11 and functional variants therefrom. The terms 'catalytic domain of PKG-I$\beta$_ refer to the sequence SEQ ID NO: 12 and functional variants therefrom.

As serine/threonine kinases, PKG-I and PKG-I$\beta$ catalyze the transfer of phosphate from ATP, that is to say catalyze the phosphorylation, on serine or threonine residues in a large number of substrates, among which histone H2B.

In the context of the invention, the functional variants of SEQ ID NO: 11 encompass peptides which sequence derives from the sequence SEQ ID NO: 11 by insertions, substitutions, and/or deletion, of amino-acid residues at one or more positions of the sequence of reference, and which have retained the ability to catalyze phosphorylate serine/threonine residues of PKG-I substrates, preferably of H2B. Of particular interest are the functional variants which sequence contains conservative substitutions, that is to say wherein amino acids residues of the sequence SEQ ID NO: 11 are substituted for other amino acid residues with similar chemical properties (e.g., charge or hydrophobicity) and therefore do not change the functional properties of the molecule. Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of SEQ ID NO: 11 is a peptide which sequence derives from the sequence SEQ ID NO: 11 by one or more conservative substitutions. Yet preferably, a functional variant of SEQ ID NO: 11 has a sequence which has at least 80, 85, 90 or 95% identity with the sequence SEQ ID NO: 11. In a preferred embodiment, a functional variant of SEQ ID NO: 11 has a sequence which has at least 80, 85, 90 or 95% identity with the sequence SEQ ID NO: 11 and is a peptide which sequence derives from the sequence SEQ ID NO: 11 by conservative substitutions.

In the context of the invention, the functional variants of SEQ ID NO: 12 encompass peptides which sequence derives from the sequence SEQ ID NO: 12 by insertions, substitutions, and/or deletion, of amino-acid residues at one or more positions of the sequence of reference, and which have retained the ability to catalyze phosphorylate serine/threonine residues of PKG-I$\beta$ substrates, preferably of H2B. Of particular interest are the functional variants which sequence contains conservative substitutions, that is to say wherein amino acids residues of the sequence SEQ ID NO: 12 are substituted for other amino acid residues with similar chemical properties (e.g., charge or hydrophobicity) and therefore do not change the functional properties of the molecule. Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of SEQ ID NO: 12 is a peptide which sequence derives from the sequence SEQ ID NO: 12 by one or more conservative substitutions. Yet preferably, a functional variant of SEQ ID NO: 12 has a sequence which has at least 80, 85, 90 or 95% identity with the sequence SEQ ID NO: 12. In a preferred embodiment, a functional variant of SEQ ID NO: 12 has a sequence which has at least 80, 85, 90 or 95% identity with the sequence SEQ ID NO: 12 and is a peptide which sequence derives from the sequence SEQ ID NO: 12 by conservative substitutions.

The capacity to catalyze phosphorylate serine/threonine residues of PKG-I substrates, in particular of H2B, may easily be determined using standard methods known in the part, such as those disclosed by Glass and Krebs (*J Biol Chem;* 254:9728-9738, 1979).

In the context of the invention, the terms 'functional variants_ when referring to the polypeptide of the invention encompass polypeptides which sequence derives from the sequence of the polypeptide of the invention by insertions, substitutions, and/or deletion, of amino-acid residues at one or more positions of the sequence of reference, and which have retained the ability to bind cGMP. The binding of cGMP to a given polypeptide may easily be determined by methods known in the art, such as detailed in Dotsmann et al.

Preferably, a functional variant of the polypeptide of the invention is a peptide which sequence derives from the sequence of the polypeptide of the invention by one or more conservative substitutions. Yet preferably, a functional variant of the polypeptide of the invention has a sequence which has at least 80, 85, 90 or 95% identity with the sequence of said polypeptide. In a preferred embodiment, a functional variant of the polypeptide of the invention has a sequence which has at least 80, 85, 90 or 95% identity with the sequence of said polypeptide and is a peptide which sequence derives from the sequence of the polypeptide of the invention by conservative substitutions.

In the sense of the present invention, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman, by means of the similarity search method of Pearson and Lipman (1988) or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P). The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid, nucleotide or residue is identical between the two sequences, preferably between the two complete sequences, dividing the number of identical positions by the total number of positions in the alignment window and multiplying the result by 100 to obtain the percentage identity between the two sequences.

Preferably, the invention also pertains to modified polypeptides, which are derived from the polypeptide of the invention or its functional variants by introduction of chemical modification into one or more amino acid residues, peptide bonds, N- and/or C-terminal ends of the protein, aimed at increasing the stability, bioavailability or bioactivity of the protein, as long as the modified polypeptide remains functional.

The polypeptide of the invention may further be functionalized with peptide sequences having properties of interest, such as peptide signals, which are localization sequences that will enable targeting the polypeptide of the invention to specific subcellular compartment, or fluorescent peptides, that will be useful for in vitro detection of the polypeptide.

Peptides signals are peptides capable of targeting a polypeptide to a specific subcellular compartment, and are well known in the art. Of particular interest are the sequences capable of targeting peptides to the plasma membrane, and more particularly to lipid rafts. Lipid rafts are sphingolipid- and cholesterol-rich plasma membrane microdomains, which have been identified and proposed to function as platforms where signal transduction molecules may interact with receptors.

Advantageously, the polypeptide of the invention comprises a peptide signal. Preferably the peptide signal is capable of targeting the polypeptide of the invention to specific subcellular compartments, more preferably to the plasma membrane, yet preferably to lipid rafts.

Peptide signals capable of targeting a peptide to the plasma membrane are well known in the art. For instance, the N terminus domains of proteins from the Src family, and in particular the peptide of sequence SEQ ID NO: 13, which corresponds to the palmitoylation and myristoylation motifs of the N terminus part of the Lyn Kinase, have been shown to enable the localization of said proteins to lipid rafts. In contrast, the peptide of sequence SEQ ID NO: 14, which corresponds to the CaaX-polylysine motif derived from the protein K-Ras, is known to target proteins to the plasma membrane while restricting the localization to lipid rafts. These sequences may be used as peptide signal either alone or in tandem repeat.

Preferably, in the polypeptide of the invention, the peptide signal comprises or consists of the sequence SEQ ID NO: 13 or 14, more preferably the sequence SEQ ID NO: 13, or functional variants therefrom. Advantageously, in the polypeptide of the invention, the peptide signal comprises or consists of tandem repeats of the sequence SEQ ID NO: 13, or functional variants therefrom.

In the context of the invention, the functional variants of SEQ ID NO: 13 encompass peptides which sequence derives from the sequence SEQ ID NO: 13 by insertions, substitutions, and/or deletions of amino-acid residues at one or more positions of the sequence of reference, and which have retained the ability to allow the localization of a peptide bound thereto or comprising thereof to lipid rafts. Of particular interest are the functional variants which sequence contains conservative substitutions, that is to say wherein amino acids residues of the sequence SEQ ID NO: 13 are substituted for other amino acid residues with similar chemical properties (e.g., charge or hydrophobicity) and therefore do not change the functional properties of the molecule. Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of SEQ ID NO: 13 is a peptide which sequence derives from the sequence SEQ ID NO: 13 by one or more conservative substitutions. Yet preferably, a functional variant of SEQ ID NO: 13 has a sequence which has at least 80, 85, 90 or 95% identity with the sequence SEQ ID NO: 13. In a preferred embodiment, a functional variant of SEQ ID NO: 13 has a sequence which has at least 80, 85, 90 or 95% identity with the sequence SEQ ID NO: 13 and is a peptide which sequence derives from the sequence SEQ ID NO: 13 by conservative substitutions.

In the context of the invention, the functional variants of SEQ ID NO: 14 encompass peptides which sequence derives from the sequence SEQ ID NO: 14 by insertions, substitutions, and/or deletion, of amino-acid residues at one or more positions of the sequence of reference, and which have retained the ability to allow the localization of a peptide bound thereto or comprising thereof to the cellular membrane, at the exclusion of lipid rafts. Of particular interest are the functional variants which sequence contains conservative substitutions, that is to say wherein amino acids residues of the sequence SEQ ID NO: 14 are substituted for other amino acid residues with similar chemical properties. (e.g., charge or hydrophobicity) and therefore do not change the functional properties of the molecule). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of SEQ ID NO: 14 is a peptide which sequence derives from the sequence SEQ ID NO: 14 by one or more conservative substitutions. Yet preferably, a functional variant of SEQ ID NO: 14 has a sequence which has at least 80, 85, 90 or 95% identity with the sequence SEQ ID NO: 14. In a preferred embodiment, a functional variant of SEQ ID NO: 14 has a sequence which has at least 80, 85, 90 or 95% identity with the sequence SEQ ID NO: 14 and is a peptide which sequence derives from the sequence SEQ ID NO: 14 by conservative substitutions.

The capacity of a peptide signal to allow the localization of a peptide bound thereto or comprising thereof to the cellular membrane, and in particular to lipid rafts or at the exclusion of lipid rafts may easily be determined using standard methods, in particular based on fluorescence microscopy and/or density gradients, such as detailed in the experimental part of the present application.

The peptide signal may be in C terminus or in N terminus of the polypeptide of the invention. Preferably, the peptide signal is in N terminus of the polypeptide of the invention.

The polypeptide of the invention may further be functionalized with fluorescent peptides, that will be useful for in vitro detection of the polypeptide.

Fluorescent peptides are well known in the art. Examples of fluorescent peptides are the green fluorescent protein (GFP), or GFP variants such as cyan fluorescent protein (CFP), yellow fluorescent protein (YFP) and red fluorescent protein (RFP) and their variants such as the optimized CFP Turquoise or the YFP variant Venus. Advantageously, the polypeptide of the invention further comprises a fluorescent peptide, preferably chosen in the list consisting of green fluorescent protein (GFP), cyan fluorescent protein (CFP), yellow fluorescent protein (YFP) and red fluorescent protein (RFP), and their variants such as the optimized CFP Turquoise or the YFP variant Venus.

Another aspect of the invention relates to a polynucleotide encoding the polypeptide of the invention, and a recombinant vector comprising said polynucleotide.

In the context of the invention, the term 'polynucleotide_ refers to a polydeoxyribonucleotides or polyribonucleotides, in the form of a separate fragment or a larger construct, and includes DNA, cDNA and RNA sequences which encode the polypeptide of the invention. Preferably, the polynucleotide of the invention is an isolated polynucleotide. The term 'isolated_ as used herein includes polynucleotides substantially free of other nucleic acids, proteins, lipids, carbohydrates or other materials with which it is naturally associated.

Preferably, said recombinant vector is an expression vector capable of expressing said polynucleotide when transfected or transformed into a host cell such as a eukaryotic or prokaryotic cell like a mammalian, bacterial or fungal cell. 'Expression vectors_ are DNA sequences that are required for the transcription of cloned DNA and the translation of their mRNAs in an appropriate host. An appropriately constructed expression vector may contain: an origin of replication for autonomous replication in host cells, selectable markers, a limited number of useful restriction enzyme sites, a potential for high copy number, and active promoters. Suitable selectable markers may for instance be chosen among the genes encoding neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for S. cerevisiae. Some expression vectors do not contain an origin of replication for autonomous replication in host cells but rather depend on the ability of the vector to stably integrate (either randomly or by a homologous integration event) using a marker to select for integration/maintenance. A promoter is defined as a DNA sequence that directs RNA polymerase to bind to DNA and initiate RNA synthesis. A strong promoter is one which causes mRNAs to be initiated at high frequency. The polynucleotide is inserted into the expression vector in proper orientation and correct reading frame for expression. Preferably, the polynucleotide is operably linked to at least one transcriptional regulatory sequence and, optionally to at least one translational regulatory sequence. Such vectors comprise YAC (yeast artificial chromosome), BAC (bacterial artificial), baculovirus vectors, phage, phagemid, cosmid, viral vector, plasmid, RNA vector or a linear or circular DNA or RNA molecule which may consist of chromosomal, non-chromosomal, semi-synthetic or synthetic DNA. Suitable vectors according to the present invention comprise, but are not limited to, YAC (yeast artificial chromosome), BAC (bacterial artificial), baculovirus vectors, phage, phagemid, cosmid, viral vector, plasmid, RNA vector or a linear or circular DNA or RNA molecule which may consist of chromosomal, non-chromosomal, semi-synthetic or synthetic DNA. Suitable plasmids to be used a mammalian expression vectors include but are not limited to, pcDNA3, pcDNA3.1, pcDNAI, pcDNAIamp (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and ≅ZD35 (ATCC 37565). Suitable plasmids to be used as bacterial expression vectors include but are not limited to pCR2.1 (Invitrogen), pET11a (Novagen), lambda gt1 1 (Invitrogen), pcDNAII (Invitrogen), pKK223-3 (Pharmacia), and pQE vectors (Qiagen) including pQE70, pQE60, pQE-9. Suitable plasmids to be used as expression vectors in fungal cells include but are not limited to pYES2 (Invitrogen), Pichia expression vector (Invitrogen). Suitable plasmids to be used as expression vectors in insect cell include but are not limited to pBlueBacIII, pBlueBacHis2 (Invitrogen) and pFastBac1, pFastBacHT (Life Technologies). Viral vectors include retrovirus, adenovirus, parvovirus (e.g., adenoassociated viruses), coronavirus, negative strand RNA viruses such as ortho-myxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus. Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses.

Another aspect of the invention provides a host cell or a non-human organism transformed with said polynucleotide or recombinant vector. The non-human transgenic organism is obtained from a unicellular or pluricellular microorganism or a higher eukaryotic organism. The expression vector may be introduced into host cells via any one of a number of techniques including but not limited to infection, transformation, transfection, lipofection, protoplast fusion, and electroporation. Modified host cells containing the expression vector may be clonally propagated and individually analyzed to determine whether they produce the polypeptide of the invention.

In a preferred embodiment said modified host cell is a eukaryotic cell such as a human cell. In another embodiment, said non-human transgenic organism is a transgenic plant, nematode, zebrafish or algae.

The polynucleotide, vector, host cell, and non-human transgenic organism of the invention are useful for the production of the polypeptide/chimeric protein of the invention using well-known recombinant DNA techniques.

Another aspect of the invention relates to the non-therapeutic use of the polypeptide, polynucleotide, vector of the invention, in vitro or in vivo, as cGMP chelating agent. Preferably the invention relates to the non-therapeutic use of the polypeptide, polynucleotide, vector of the invention, for stabilizing cGMP concentration, and/or for inhibiting cGMP signalization in vivo and/or in vitro. Yet preferably, the non-therapeutic use, when performed in vivo, is performed in a healthy subject.

The terms 'stabilizing cGMP concentration_ should be construed as generally understood in the art, that is to say as the action of minimizing the variations of the concentration of free cGMP in a composition upon addition or induction of cGMP in said composition. In the context of the invention, the terms 'concentration of free cGMP_ refer to the concentration of unbound cGMP. The variation, and in particular the increase, of cGMP concentration may easily be measured using for instance the biosensor $^ThPDE5^{VV}$, by monitoring the FRET/CFP ratio, as disclosed in the experimental part. In the context of the invention, cGMP concentration can be considered as stabilized in a composition when the FRET/CFP ratio of the biosensor $^ThPDE5^{VV}$ varies, preferably increases, of less than 10%, preferably less than 5% of the variation detected in the absence of the polypeptide, polynucleotide, vector of the invention, upon addition or induction of cGMP in said composition.

The terms 'inhibiting cGMP signal_, 'cGMP signal inhibition_ should be construed as generally understood in the art, that is to say as the action of inhibiting the downstream effectors known to be activated by cGMP as a second messenger, for instance cyclic nucleotide gated calcium channels (CNGs). The cyclic nucleotide-gated (CNG) channel of the rod photoreceptor cell plays a key role in phototransduction by controlling the flow of $Na^+$ and $Ca2^+$ into the rod outer segment (ROS) in response to light-induced changes in intracellular cGMP concentration. cGMP activates the opening of CNGs, leading to the influx of $Na^+$ and $Ca2^+$ ions through CNG channels in the cell. Methods for assessing the activation of photoreceptor channels by measuring the cGMP-activated currents at the cytoplasmic membrane using outer segment membrane patches have been thoroughly disclosed in Tanaka et al. (*Biochemistry*, 28(7): 2776-84, 1989). The inhibition of the cGMP signal may thus easily be assessed by monitoring intracellular cGMP-activated currents at the cytoplasmic membrane, in the presence of the polypeptide, polynucleotide, vector of the invention, based on such methods.

It is well documented that a number of pathologies are associated with cGMP signaling dysfunction. The polypeptide, polynucleotide, vector, and host cell of the invention, may thus be particularly useful in preventing or treating such pathologies. In this context, the polypeptide, polynucleotide, vector, or host cell of the invention, may be formulated into a composition suitable for pharmaceutical use.

Another aspect of the invention relates to a pharmaceutical composition, comprising at least one polypeptide, polynucleotide, vector, and/or host cell of the invention, and, preferably, a pharmaceutically acceptable carrier. In the context of the invention, the terms "pharmaceutically acceptable" refer to carriers which can be used in the preparation of a pharmaceutical composition which is generally safe, non-toxic and neither biologically nor otherwise undesirable, and which is acceptable for veterinary use as well as for human pharmaceutical use. Suitable vehicles or carriers include any pharmaceutically acceptable vehicle such as buffering agents, stabilizing agents, diluents, salts, preservatives, and emulsifying agents. Examples of suitable buffering agents include buffered solutes, such as phosphate buffered solution, chloride solutions or Ringers solution. Examples of suitable stabilizing agents include human serum albumin (HSA), polyvinylpyrrolidone or hyaluronic acid.

The composition of the invention may be formulated according to the intended administration route. For instance, formulations suitable for oral administration include liquid or solid formulations such as tablets, pills, powders (hard or soft gelatine capsules) or granules. Typically, in such formulations, the polypeptide, polynucleotide, vector, and/or host cell of the invention is mixed with one or more inert diluents such as starch, cellulose, sucrose, lactose or silica, in a stream of argon. These compositions may also comprise substances other than diluents, for example lubricants such as magnesium stearate or talc, coloring agent, coating (coated tablets) or varnish. Formulations suitable for injection, such as used in parenteral administration, are preferably sterile and fluid, and may preferably be aqueous or non-aqueous solutions, suspensions or emulsions.

Another aspect of the invention relates to the polypeptide, polynucleotide, vector, host cell of the invention, or composition comprising thereof, for use as a medicine, preferably for use in the prevention and/or treatment of pathologies associated with intracellular cGMP signaling dysfunction.

In the context of the invention, the terms 'pathologies associated with intracellular cGMP signaling dysfunction_ should be construed according to their general meaning in the art. Preferably, said pathologies are associated with intracellular cGMP signaling dysfunction due to an abnormally high intracellular concentration of cGMP. In the context of the invention, 'an abnormally high intracellular concentration of cGMP_ refer to an intracellular concentration of cGMP which is significantly higher than in cells from a healthy donor. Yet preferably, said pathologies are chosen in the list consisting of retinitis pigmentosa; cardiovascular diseases, preferably chosen in the list consisting of stroke, venous thrombosis or arterial thrombosis; schizophrenia; Huntington disease; achromatopia; cancer, preferably chosen in the list consisting of colorectal cancer, lung cancer, lung disease; erectile dysfunction and drug abuse.

In other terms, the invention pertains to a method for the prevention and/or treatment of pathologies associated with intracellular cGMP signaling dysfunction, wherein said pathologies are chosen in the list consisting of retinitis pigmentosa; cardiovascular diseases, preferably chosen in the list consisting of stroke, venous thrombosis or arterial thrombosis; schizophrenia; Huntington disease; achromatopia; cancer, preferably chosen in the list consisting of colorectal cancer, lung cancer, lung disease;

erectile dysfunction and drug abuse, comprising the step of administering the polypeptide, polynucleotide, vector, host cell of the invention, or a composition comprising thereof to a subject in need thereof, preferably in an effective amount. In the context of the invention, the terms 'effective amount_ means that the amount of polypeptide, polynucleotide, vector, host cell of the invention, or of a composition comprising thereof is of sufficient quantity to obtain appropriate prevention and or regression of the symptoms of the above-recited pathologies. The effective amount and dosage regimen may be determined by the attending physician based on usual clinical factors. As is well known in the medical arts, dosages for any one patient depends upon many factors, including the patient's size, body surface area, age, the particular compound to be administered, sex, time and route of administration, general health, and other drugs being administered concurrently.

The polypeptide, polynucleotide, vector, host cell of the invention, or composition comprising thereof referred to herein can be administered once or more than one time, in order to prevent or to treat a pathology as recited herein. Efficacy of the prevention and/or treatment can be monitored by periodic assessment.

The polypeptide, polynucleotide, vector, host cell of the invention, or composition comprising thereof referred to herein can be administered topically or systemically, through the known routes of administration. Preferably, the polypeptide, polynucleotide, vector, host cell of the invention, or composition comprising thereof referred to herein is administered through the enteric route, in particular by oral, sublingual, or rectal administration, or through the parenteral route, in particular by intracerebral, intramuscular, intradermal, transdermal, intraperitoneal or nasal administration.

In addition to the preceding features, the invention further comprises other features which will emerge from the following description, which refers to examples illustrating the present invention, as well as to the appended figures.

EXAMPLE 1

Constructs

Figure 1:
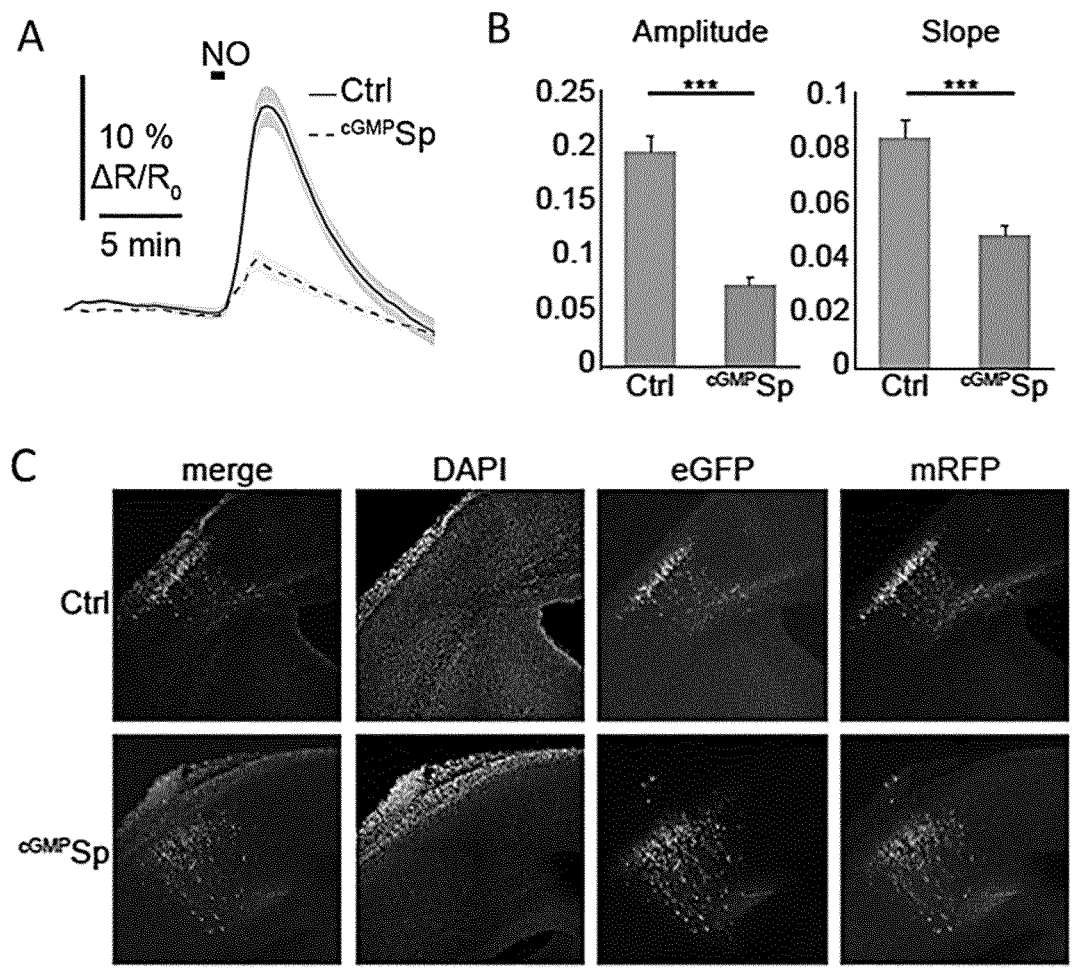
FIG. 1. The polypeptide of the invention is a cGMP scavenger and alters cortical neuron migration in vivo. (A) 1 min Spermine-NONOate (NO) exposure induces an increase in the cGMP concentration of control H293 cells, monitored by the FRET/CFP ratio from the FRET bio sensor $^{T}$hPDE5$^{VV}$. In contrast, this elevation is drastically reduced when cells express $^{cGMP}$Sp/SponGee. (B) Both the amplitude and rising speed of cGMP elevation are reduced by $^{cGMP}$Sp/SponGee expression. (C) E14.5 eGFP and mRFP co-electroporated cortical neurons are packed into a dense layer close to the marginal zone at E18.5 (top row). In contrast $^{cGMP}$Sp/SponGee-expression prevents the development of this layer, with neurons scattered throughout the depth of the developing cortex, and the formation of heterotopia at the surface of the cortex (bottom row).

A polynucleotide encoding an example of a polypeptide according to the invention, hereafter designated $^{cGMP}$Sp, cGMP Sponge, SponGee $^{or}$ $^{cGMP}$Sp/SponGee, all these terms designating the very same polypeptide, further comprising a FLAG tag in 5˜ was prepared using
the sequence SEQ ID NO: 15:

ATGAGCGAGCTGGAGGAAGACTTTGCCAAGATTCTCATGCTCAAGGAGGAG

AGGATCAAAGAGCTGGAGAAGCGGCTGTCAGAGAAGGAGGAAGAAATCCAG

GAGCTGAAGAGGAAACTCCATAAATGCCAGTCAGTGCTGCCCGTGCCCTCG

ACCCACATCGGCCCCCGGACCACCCGGGCACAGGGCATCTCGGCCGAGCCG

CAGACCTACAGGTCCTTCCACGACCTCCGAGTGACCCTGCCCTTCTACCCC

AAGAGTCCACAGTCCAAGATCGATCTCATAAAGGAGGCCATCCTTGACAAT

GACTTTATGAAGAACTTGGAGCTGTCACAGATCCAAGAGATTGTGGATTGT

ATGTACCCAGTGGAGTACGGCAAAGACAGCTGCATCATCAAAGAAGGAGAT

GTGGGGTCACTGGTGTATGTCATGGAAGATGGTAAGGTTGAAGTTACAAAA

GAAGGCGTGAAGCTGTGCACAATGGGTCCTGGTAAAGTGTTTGGAGAGTTG

GCTATCCTTTACAACTGTACCCGGACGGCGACCGTCAAAACTCTTGTAAAT

GTGAAACTCTGGGCCATTGATCGACAATGTTTTCAGACGATAATGATGAGG

ACAGGACTTATCAAGCATACCGAGTATATGGAATTTTTAAAAAGCGTTCCA

ACATTCCAGAGCCTTCCTGAAGAGATCCTCAGTAAACTTGCTGACGTCCTT

GAAGAGACCCACTATGAAAATGGGGAATATATCATCAGGCAAGGTGCAAGA

GGGGACACCTTCTTTATCATCAGTAAAGGAAAGGTTAATGTCACTCGTGAA

GACTCGCCCAATGAAGACCCAGTCTTTCTTAGAACCTTAGGAAAAGGAGAT

TGGTTTGGAGAGAAAGCCTTGCAGGGGGAAGATGTGAGAACAGCGAATGTA

ATTGCGGCAGAAGCTGTAACCTGCCTTGTGATCGACAGAGACTCTTTCAAA

CATTTGATTGGAGGATTAGATGATGTTTCTAAAAAGCATATGAAGATGCAG

AAGCTAAG in frame with a tandem repeat of the Lyn Kinase N-terminus domain encoded by the sequence SEQ ID NO: 16:

ATGGGCTGCATCAAGAGCAAGCGCAAGGACAAGATGGGCTGCATCAAGAGC

AAGCGCAAGGACAAG

The oligos were annealed and cloned into pcDNA3-mRFP in frame with the reporter sequence. Lipid-raft-excluded and cytosolic forms of the $^{cGMP}$Sp/SponGee variants were obtained by subcloning into pcDNA3 with or without the CaaX-polylysine motif of Kras encoded by the sequence SEQ ID NO: 17:

CAAGAAGAAGAAGAAGAAGAAGAGCAAGACCAAGTGCGTGATCATG respectively.

For expression on RGCs, the constructs were subcloned into pcX. $^{T}$hPDE5$^{VV}$ was targeted to the membrane microdomains using the In-Fusion HD cloning kit (Clontech) and subcloned into pcDNA3 or pcX.

The sequence of the truncated human PDE5A1 (hPDE5) was obtained by gene synthesis in the pUC57 vector (Genscript) and digested with SmaI and NheI enzymes (New England Biolabs). The Epac1 sequence was removed from the $^{T}$Epac$^{VV}$ vector (obtained from Dr Kees Jalink, NKI-AVL, Amsterdam, Netherlands) by digestion with EcoRV and NheI (New England Biolabs) and replaced by hPDE5. Cell culture: HEK293T cells were kept in a 37° C., 5% CO2 incubator and transfected using Lipofectamine 2000 (Invitrogen) according to the manufacturer's protocol and imaged the day following transfection or fixed and processed for immunocytofluorescence.

Membrane fractionation by detergent-free method: Electroporated retinas were pelleted (195 g for 5 min at 4° C.) and resuspended in 1.34 mL of 0.5 M sodium carbonate, pH 11.5, with protease inhibitor cocktail and phosphatase inhibitor cocktail 1, 2 and 3 (Sigma-Aldrich). The homogenate was sheared through a 26-gauge needle and sonicated three times for 20 s bursts. The homogenate was adjusted to 40% sucrose by adding 2.06 mL of 60% sucrose in MBS (25 mM MES, pH 6.4, 150 mMNaCl, and 250 mM sodium carbonate), placed under a 5-30% discontinuous sucrose gradient, and centrifuged at 34,000 rpm for 15-18 h at 4° C. in a Beckman SW 41Ti rotor. Nine fractions (1.24 mL each) were harvested from the top of the tube mixed with 9 volumes of MBS, and centrifuged at 40,000 rpm for 1 h at 4° C. (Beckman SW-41Ti rotor). Supernatants were discarded, and membrane pellets were resuspended in 100 µl of 1% SDS.

For immunoblotting, samples were separated on 4-15% Mini-Protean TGX Tris-Glycine-buffer SDS PAGE (Biorad) and transferred onto 0.2 µm Trans-Blot Turbo nitrocellulose membranes (Biorad). Membranes were blocked for one hour at room temperature in 1×TBS (10 mMTris pH 8.0, 150 mMNaCl,) supplemented with 5% (w/v) dried skim milk powder. Primary antibody incubation was carried out overnight at 4° C., with the following antibodies: rabbit anti-GFP (1/200; A11122; Life Technologies), rabbit anti-DsRed (1/200; 632476; Clontech), rabbit anti-$\beta$-Adaptin (1/200; sc-10762; Santa Cruz) and rabbit anti-Caveolin (1/500; 610060; BD Transduction Laboratories). A goat anti-rabbit-HRP coupled secondary antibody was used for detection (Jackson ImmunoResearch, West Grove, Pa.). After antibody incubations, membranes were extensively washed in TBS T (TBS containing 2.5% Tween-20). Western blots were visualized using the enhanced chemiluminescence method (ECL prime Western Blotting detection reagent, Amersham).

Collapse assay: Retinas of E14 mice were electroporated with mRFP, Lyn-$^{cGMP}$Sp/SponGee, $^{cGMP}$Sp/SponGee or $^{cGMP}$Sp/SponGee-Kras using two poring pulses (square wave, 175V, 5 ms duration, with 50 ms interval) followed by four transfer pulses (40V, 50 ms and 950 ms interpulse). Retinas were dissected and kept 24 hours in culture medium (DMEM-F12 supplemented with glutamine (Sigma Aldrich), penicillin/streptomicin (Sigma Aldrich), BSA (Sigma Aldrich) and glucose), in a humidified incubator at 37° C. and 5% CO2. The day after, they were cut into 200 µm squares with a Tissue-Chopper (McIlwan) and explants were plated on glass coverslips coated with poly-L-lysine and Laminin (Sigma Aldrich). Cells were cultured for 24 hours in culture medium supplemented with 0.4% methyl cellulose and treated with rmSlit-1 (R&D Systems) for 1 hour.

Immunodetection

Retinal explants, or HEK cells coexpressing the targeted versions of SponGee and GFP, were fixed with 4% PFA in PB for 30 minutes, permeabilized and blocked and with 1% Triton and 3% BSA in PBS, then incubated with antobodies agains DsRed (Clontech, lot #1306037, previously used in a similar assay, (Averaimo et al., *Nat Commun.,* 7:12896, 2016) followed by a secondary antibody coupled to AlexaFluor 594 (Life Technologies) and GFP (Life Technologies, lot #1789911, previously validated in Nicol et al., *Nat. Neurosci:,* 10: 340-347, 2007) or -Tubulin (Sigma, lot #T6199, previously validated in Nicol et al., *Nat. Neurosci:,* 10: 340-347, 2007) followed by a secondary antibody coupled to AlexaFluor 488 (Life Technologies).

Imaging: Images were acquired with an inverted DMI6000B epifluorescence microscope (Leica) coupled to a 40× oil-immersion objective (N.A. 1.3) and the software Metamorph (Molecular Devices). For live imaging experiments, cells were perfused with HBS buffer with 0.2 or 2 mM CaCl. Thapsigargin was used at 1 mM). Images were acquired simultaneously for the CFP (483/32 nm) and YFP (542/27) channels every 20 seconds. Images were processed in ImageJ, corrected for background and bleedthrough and then the ratio CFP/YFP was calculated. Confocal images were acquired with a 63× oil immersion objective (N.A. 1.45) and a Z-stack containing the whole specimen was sampled at nyquist frequency. Images were rendered in ImageJ and Photoshop.

Animals: Pregnant C57BL6/J and RjOrl:SWISS mice and Sprague-Dawley rats were purchased from Janvier Labs. All animal procedures were performed in accordance with institutional guidelines and approved by local ethics committees (C57BL6/J mice, C2EA-05: Comité d'éthique en experimentation animale Charles Darwin; Sprague-Dawley rats, ethics committee C2EA-59: Comité d'éthique en matière d'expérimentation animale Paris Centre et Sud). Animals were housed under 12 h light/12 h dark cycle. Embryos from dated matings (developmental stage stated in each section describing individual experiments) were not sexed during the experiments and the female over male ratio is expected to be close to 1.

Cell Death Assay

HEK293 Cells were plated on poly-lysine-coated coverslips and transfected the following day with a pCX-mRFP or a pCX-SponGee vector using Lipofectamine 2000 (Thermo Fisher) following the manufacturers instructions. Three days after plating, cells were either fixed with 4% paraformaldehyde and processed for immunocytochemistry with the antibodies against Cleaved Caspase 3 (Asp175; Cell Signaling; lot #0043) and -tubulin (Sigma) or treated with the CellEvent Caspase 3/7 Green Detection Reagent (Thermo Fisher) for 30 minutes and then fixed and labeled with an -tubulin antibody. For each experiment, the proportion of Caspase3-positive over unlabeled cells in the population of mRFP- or SponGee-positive cells was computed from 10 randomly chosen fields acquired on a 20× air objective in a DM6000 microscope (Leica Microsystems).

Rat Hippocampal Culture

Hippocampal neuronal cultures were performed essentially as described previously (Leterrier et al., *J. Neurosci.,* 26: 3141-3153, 2006). Briefly, hippocampi of rat embryos were dissected at embryonic day 18. After trypsinization, dissociation was achieved with a fire-polished Pasteur pipette. Cells were counted and plated on poly-D-lysine-coated 18-mm diameter glass coverslips, at a density of 300-400 cells·mm$^{-2}$. The plating medium was Neurobasal (Life Technologies) supplemented with 2% B27 (Life Technologies) and containing stabilized Glutamine (0.5 mM) and penicillin G (10 U·ml$^{-1}$)/streptomycin (10 g·ml$^{-1}$). Four hours after plating, the coverslips were transferred into Petri dishes containing supplemented Neurobasal medium that had been conditioned for 24 h on an 80% confluent glia layer. Neurons were transfected after 6 days in vitro (DIV) using Lipofectamine 2000 (Life Technologies), following the manufacturers instructions.

In Utero Electroporation

Timed pregnant females (Janvier Labs) were delivered to the animal facility a week prior to the surgery in order to allow a minimum of 5-days adaptation. In utero electroporation was performed as described previously (Loulier et al., *PLoS Biol.,* 7: e1000176, 2009). E14.5 females were anesthetized with Ketamine/Xylazine and a midline laparotomy was performed, exposing uterine horns and allowing visualization of embryos under oblique illumination. 1 ∃L of DNA containing two plasmids vectors combined 3:1 with sterile Fast Green dye (Sigma) was injected with a glass capillary pipette (75-125 ∃m outer diameter with beveled tip) driven by a INJECT+MATIC (INJECT+MATIC) microinjector into the lateral ventricle of each embryo. Two different plasmid vectors were injected simultaneously. The first was a plasmid encoding green fluorescent protein under the control of the chicken beta actin promoter (pCX-eGFP), used as a control of electroporation. The second was either a plasmid encoding red fluorescent protein (mRFP) control construct or SponGee-mRFP. The anode of 5 mm diameter tweezertrodes (Sonidel Limited) was placed above the dorsal telencephalon and four 35-V pulses of 50 ms duration were applied across the uterine sac. Following intrauterine surgery, the incision site was closed with sutures (4-0, Ethicon) and the mouse was allowed to recover in a clean cage. Mice were either euthanized 4 days after surgery to harvest E18.5 embryonic brains, or allowed to give birth for analysis at P10 postnatal stage. Embryonic brains were dissected out, immersed overnight in Antigenfix (Diapath) fixative solution and rinsed in PBS prior to sectioning. P10 mice were deeply anesthetized with sodium pentobarbital (150 mg·kg$^{-1}$), perfused transcardially with Antigenfix (Diapath), brains dissected out and postfixed overnight in the same solution. Embryonic and postnatal brain samples were sectioned at 200 ∃m thickness on a vibrating blade microtome (Leica VT 1000S). Finally, sections were either mounted in Vectashield+Dapi (Vector laboratories) or incubated 2 hours in 10 µg·mL$^{-1}$ bis-benzimide (Sigma Aldrich) and mounted in Mowiol 4-88 (Sigma Aldrich). Confocal images were acquired with a 10× objective (N.A. 0.4) and a Z-stack containing the whole specimen was sampled at Nyquist frequency. Images were rendered in ImageJ and Photoshop.

FRET Imaging and Analysis (HEK Cells)

Images were acquired with an inverted DMI6000B epifluorescence microscope (Leica) coupled to a 40× oil-immersion objective (N.A. 1.3) and the software Metamorph (Molecular Devices). For live imaging experiments, cells transfected with $^7$hPDE5$^{VV}$ or H147, and co-expressing mRFP or SponGee were perfused with 1 mM $CaCl_2$, 0.3 ≈M $MgCl_2$, 0.5 mM $Na_2HPO_4$, 0.5 mM $NaH_2PO_4$, 0.4 ≈M $MgSO_4$, 4.25 mM KCl, 14 ≈M $NaHCO_3$, 120 mM NaCl, 0.0004% $CuSO_4$, 1.24 ≈M Fe $(NO_3)3$, 1.5 ≈M $FeSO_4$, 1.5 ≈M thymidine, 0.51 mM lipoic acid, 1.5 mM $ZnSO_4$, 0.5 ≈M sodium pyruvate (all from Sigma), 1× MEM Amino Acids (Life Technologies), 1× non-essential amino acids (Life Technologies), 25 mM HEPES (Sigma), 0.5 mM putrescine (Sigma), 0.01% BSA (Sigma), 0.46% glucose (Sigma), 1 mM glutamine (Life Technologies), 2% penicillin streptomicin (Life Technologies). Vitamin B12 and riboflavin were omitted because of their autofluorescence. SpermineNONOate was used at 50 μM, ODQ (Tocris) at 10 μM and Forskolin (Sigma) at 10 μM. Images were acquired simultaneously for the CFP (483/32 nm) and YFP (542/27) channels every 20 seconds. Images were processed in ImageJ, corrected for background and bleedthrough and then the ratio CFP/YFP was computed. Confocal images were acquired with a 63× oil immersion objective (N.A. 1.45) and a Z-stack containing the whole specimen was sampled at Nyquist frequency. Images were rendered in ImageJ and Photoshop.

FRET Imaging (Rat Hippocampal Cultures)

Neurons transfected with $^7$hPDE5$^{VV}$ probe were imaged by videomicroscopy between DIV8 and DIV11 on a motorized Nikon Eclipse Ti-E/B inverted microscope with the Perfect Focus System (PFS) in a 37° C. thermostated chamber, using an oil immersion CFI Plan APO VC 60×, NA 1.4 objective (Nikon). Acquisitions were carried out at the excitation wavelength of the CFP (434 nm+/−15 nm) using an Intensilight (Nikon). Emitted light passed through an Optosplit II beam-splitter (Cairn Research) equipped with a FF509-FDi01 dichroic mirror, a FF01-483/32-25 CFP filter and a FF01-542/27-25 YFP filter and was collected by an EM-CCD camera (Evolve 512, Photometrics), mounted behind a 2× magnification lens. Acquisitions were performed by piloting the set-up with Metamorph 7.7 (Molecular Devices). All filter sets were purchased from Semrock. Cultured neurons on 18-mm coverslips were placed in a closed imaging chamber containing an imaging medium: 120 mM NaCl, 3 mM KCl, 10 mM HEPES, 2 mM $CaCl_2$, 2 mM $MgCl_2$, 10 mM D-glucose, 2% B27, 0,001% BSA. The acquisition lasted 70 minutes registering one image every 2 minutes, registering in parallel 4 to 6 neurons on the same coverslip. 30 minutes after the beginning of the acquisition, vehicle solution or ODQ 100 μM (R&D Systems) was applied 40 minutes after the onset of acquisition, DEA NONOate (Sigma) 50 μM or Forskolin (Sigma) 10 μM was applied.

FRET Data Analysis (Rat Hippocampal Culture)

Images were divided in two parts on ImageJ to separate the CFP channel from the YFP channel. Data were then analyzed on Matlab by calculating the FRET ratio at each time point for one or several Regions Of Interest (ROIs). The user defined ROIs for each position. For each image, the value of the FRET ratio corresponds to (IY-BY)/(IC-BC), where IY is the mean intensity of the ROI in the YFP channel; BY is the mean intensity of the background in the YFP channel; IC is the mean intensity of the ROI in the CFP channel; BC is the value of the background in the CFP channel. For each ROI, the FRET ratio was then normalized by the baseline mean, defined as the 7 time points before first treatment injection. FRET Ratio=100*(Rc−Ro)/Ro, where Rc is the value of the crude FRET ratio and Ro is the mean of the baseline. The quantitative results obtained for each neuronal compartment were grouped together and the mean FRET ratio normalized to baseline and SEM were calculated for each time point. Deviation was corrected for somata and dendrites on Matlab. The mean slope was calculated for all neurons in the somata and dendrites, respectively, for the last 7 time points before addition of treatment and subtracted from all FRET ratio time points.

Analysis and Statistics

No data were excluded from the analysis. No sample size calculation was performed. Sample size was considered sufficient after three reproducible and independent experiments, leading to n ℏ3 since several animals, coverslips, or biochemical assays were often analyzed for the same experimental condition. Animals or cultures were equivalent and not distinguishable one from another before treatment, de facto randomizing the sample without the need of a formal randomization process. Photomicrographs were often easily traceable by eye to its experimental condition, making blind analysis of the data difficult to achieve. When careful blinding was performed, experiments reproduced the results obtained in non-blinded experiments with identical experimental conditions. Image calculation and analysis were performed using ImageJ, except for the validation of the $^7$hPDE5$^{VV}$ sensor for which Matlab was used. Statistical tests were calculated using GraphPad Prism (GraphPad Software Inc.).

Results

An example of a polypeptide according to the invention (herein designed $^{cGMP}$Sp, cGMP Sponge, SponGee or $^{cGMP}$Sp/SponGee) was designed based on a high affinity chimeric variant of cGMP-dependent Protein Kinase (PKG) containing portions of PKG-I and PKG-Iβ. $^{cGMP}$Sp/SponGee contains the binding sites and the chimeric affinity domain and excludes the kinase domain to prevent the activation of downstream effectors (FIG. 1). This construct was further fused to the fluorescent protein mRFP for easy identification of $^{cGMP}$Sp/SponGee-expressing cells.

The buffering properties of $^{cGMP}$Sp/SponGee were tested with $^7$hPDE5$^{VV}$, a FRET sensor for cGMP based on the human version of PDE5 fused to an optimized CFP (Turquoise) and a tandem of a YFP variant (Venus) as the FRET donor and acceptors, respectively. $^7$hPDE5$^{VV}$ is similar to cGES-DE5, a previously described cGMP biosensor (Nikolaev et al., Nat. Methods., 3: 23-25, 2006). The donor and acceptor fluorescent proteins of cGES-DE5 have been replaced by their optimized variants mTurquoise and a tandem of mVenus respectively, following a previously described strategy (Klarenbeek et al., PLoS ONE 6, e19170, 2011). $^7$hPDE5$^{VV}$ was expressed in vitro in rat hippocampal neurons exposed to DEA-NONOate, a donor of NO, which activates cGMP synthesis by soluble guanylyl cyclases (Bhargava et al., *Front Mol Neurosci.*, 6, 26, 2013).

Monitoring the FRET over CFP ratio in $^T$hPDE5$^{VV}$-expressing cells reflects the intracellular variation in cGMP concentration. H293 cells exhibit an increase in the FRET over CFP ratio when exposed to a short pulse of Spermine-NONOate, a donor of NO, which in turn activates cGMP synthesis by soluble guanylyl cyclases, revealing an increase in intracellular cGMP concentration. Cells were exposed to a sustained Spermine-NONOate stimulation at the end of the experiment to induce a massive cGMP synthesis and control their viability. A 1 minute pulse of Spermine-NONOate induced a 20% increase in the FRET/CFP ratio with a 1 minute delay since the start of the stimulation. This delay is partially explained by the dead volume in the perfusion line. Expressing $^{cGMP}$Sp/SponGee largely reduced the Spermine-NONOate-induced FRET/CFP change, reflecting a reduction of cGMP molecules available to the bind the biosensors. This observation demonstrate that $^{cGMP}$Sp/SponGee is a cGMP scavenger and reduces the availability of this second messenger for its downstream pathways. The $^{cGMP}$Sp/SponGee-induced reduction in the FRET/CFP elevation was less marked with longer (2 minutes) Spermine-NONOate exposure, suggesting that prolonged increase in cGMP concentration leads to the saturation of the cGMP binding sites.

To evaluate $^{cGMP}$Sp/SponGee capability to interfere with a physiological process in vivo and thus its potential to be used as a tool to investigate cellular function in an intact organism, $^{cGMP}$Sp/SponGee was electroporated in utero in the lateral brain ventricle of E14.5 mice embryos. The migration of electroporated cortical neurons was analyzed at gestational day 18. In E18 eGFP and mRFP co-electroporated animals, neurons display an archetypical migration with the majority of transfected cells accumulated at the cortical plate near the marginal zone (FIG. 1). In contrast, neurons co-electroporated with $^{cGMP}$Sp/SponGee-mRFP and GFP exhibit a delayed migration, with numerous neurons lost throughout the neocortex, including the subventricular zone. Furthermore, several electroporated cells failed to stall at the cortical plate, overshooting towards the marginal zone. This demonstrates that cGMP buffering by $^{cGMP}$Sp/SponGee is sufficient to alter the physiological cGMP modulation required for the sound neuronal migration in vivo.

Figure 2:
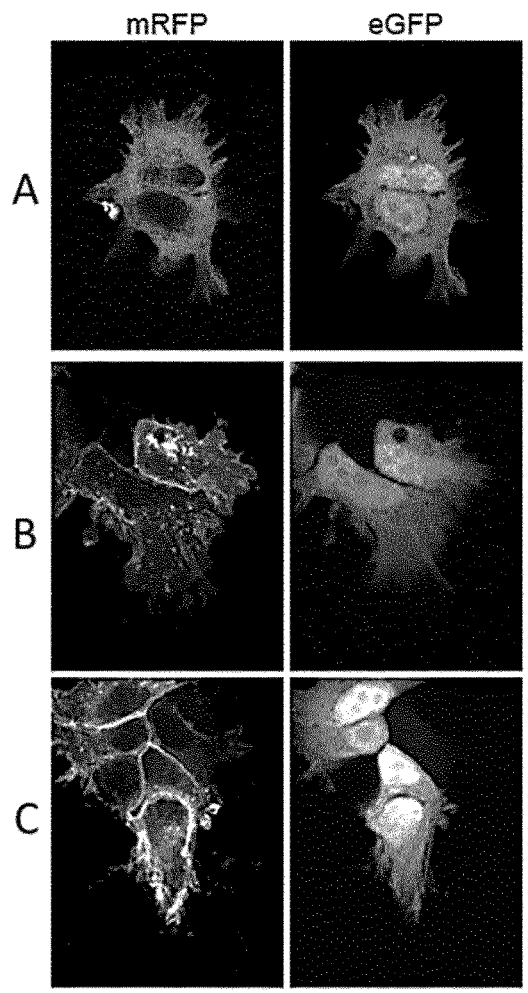
FIG. 2. Subcellular restriction of cGMP manipulation using the polypeptide of the invention $^{cGMP}$Sp/SponGee. A: subcellular localization of $^{cGMP}$Sp/SponGee, B: subcellular localization of Lyn-$^{cGMP}$Sp/SponGee, C: subcellular localization of $^{cGMP}$SP/SponGee-Kras. $^{cGMP}$Sp/SponGee was either used to globally alter cGMP signaling when not targeted to any cellular compartment or to target specific compartments. Lyn-$^{cGMP}$SP/SponGee aims to target to lipid rafts whether $^{cGMP}$Sp/SponGee-Kras is intended to be restricted to the non-raft fraction of the plasma membrane. (A) $^{cGMP}$Sp/SponGee was detected in the cytoplasm (top row) whether both Lyn-$^{cGMP}$Sp/SponGee and $^{cGMP}$Sp/SponGee p-Kras were found at the plasma membrane (middle and bottom row).
Figure 3:
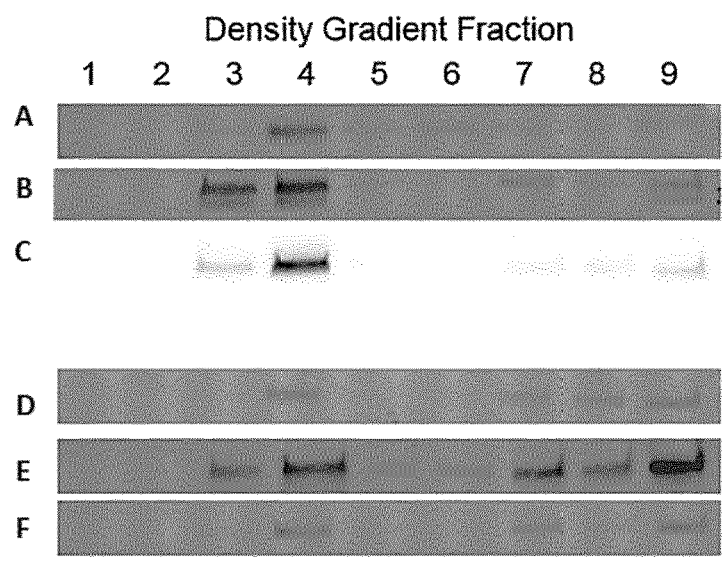
FIG. 3. Plasma membrane fractionation highlighted distinct subcellular localization of Lyn-$^{cGMP}$Sp/SponGee and $^{cGMP}$Sp/SponGee-Kras. A: Caveolin, B: Lyn-T $^{T}$hPDE5$^{VV}$, C: Lyn-$^{cGMP}$Sp/SponGee, D: Adaptin, E: T $^{T}$hPDE5$^{VV}$-Kras, F: $^{cGMP}$Sp/SponGee-Kras. Lyn-$^{cGMP}$Sp/SponGee was highly enriched in fraction 3 whether the localization of $^{cGMP}$Sp/SponGee-Kras was shifted towards higher density fractions (4 to 9).
Figure 4:
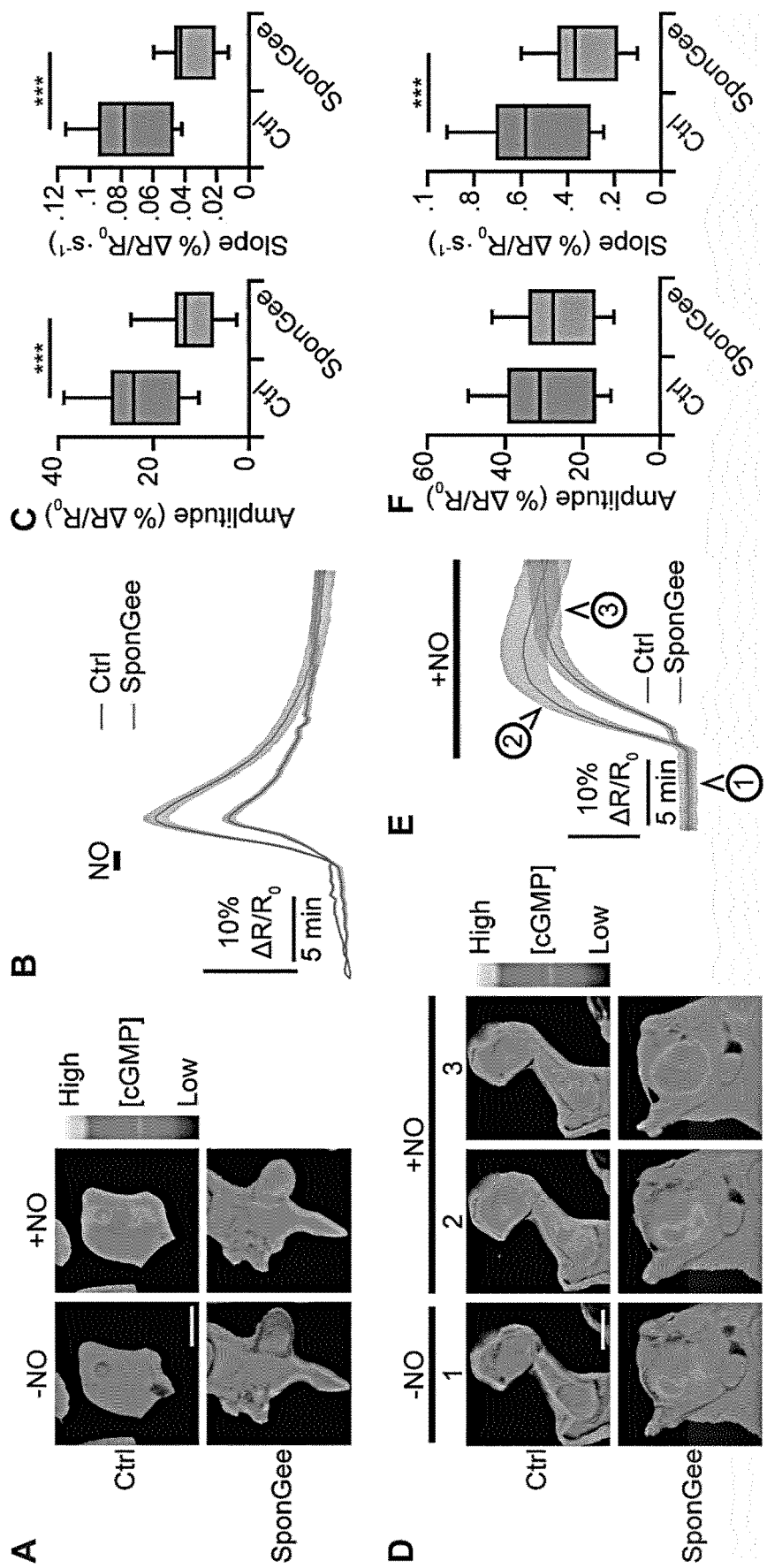
FIG. 4. SponGee reduces the elevation of cGMP concentration induced by a prolonged pulse of Spermine-NONOate and delays massive and sustained elevation of intracellular cGMP concentration. (A-C) HEK293 cells were exposed to a 2 min pulse of spermine-NONOate. $^{cGMP}$Sp/SponGee-expressing cells display a reduction of both the FRET:CFP ratio amplitude and the rate of increase compared to controls. (D-F) A 15 min pulse of Spermine-NONOate induces a massive change in the $^{T}$hPDE5$^{VV}$ FRET:CFP ratio. Cells expressing $^{cGMP}$Sp/SponGee exhibit a change in the FRET: CFP ratio of similar magnitude, but delayed as compared to cells devoid of SponGee. Scale bar, 20 µm. (B,E) Data are mean±s.e.m. (C,F) Box-and-whisker plot elements: center line, mean; box limits, upper and lower quartiles; whiskers, s. d. *** P≤0.001; Mann-Whitney test.

Guanylyl cyclases, the cGMP-synthesizing enzymes, are restricted in subcellular compartments leading to compartmentalization of cGMP signals within cells. Since genetic-encoding confers the ability to restrict the expression of the constructs to a specific organelle using targeting sequences, the functionality of $^{cGMP}$Sp/SponGee was assessed in this scenario. The cGMP buffer was targeted to the membrane, its expression being further restricted to the lipid raft microdomain by the N-Terminus fusion of a tandem of palmitoylation-myristoylation targeting peptides from Lyn Kinase (Lyn-$^{cGMP}$Sp/SponGee), or being further excluded from the lipid raft domain by the C-Terminus fusion of the CaaX-polylysine motif derived from K-Ras ($^{cGMP}$Sp/SponGee-Kras). Lyn-$^{cGMP}$Sp/SponGee and $^{cGMP}$Sp/SponGee-Kras expression was restricted to the membrane, in contrast to $^{cGMP}$Sp/SponGee (FIG. 2). The localization of Lyn-$^{cGMP}$Sp/SponGee and $^{cGMP}$Sp/SponGee-Kras in distinct membrane compartments was analyzed using membrane fractionation in a density gradient. Lyn-$^{cGMP}$Sp/SponGee expression was restricted to the low density fractions 3-4, concomitant with the lipid raft marker Caveolin. In contrast, $^{cGMP}$Sp/SponGee-Kras was enriched in the high density fractions 7 to 9 together with ƒ-Adaptin, a marker of the non-raft component of the membrane. To assess whether the compartmentalized variants of $^{cGMP}$Sp/SponGee affect differentially cGMP-dependent cellular responses, the response of retinal ganglion cell growth cones expressing either Lyn-$^{cGMP}$Sp/SponGee or $^{cGMP}$Sp/SponGee-Kras to the axon guidance molecules slit-1 and ephrinA5, a process requiring cGMP, was analyzed. In untransfected axons, slit-1 and ephrin-A5 induced the collapse of the growth cone. The expression of $^{cGMP}$Sp/SponGee in the cytosol abolished the collapse response induced by both cues, confirming the requirement of cGMP signaling in this process. Similarly, slit1 and ephrinA5 failed to induce growth collapse in Lyn-$^{cGMP}$Sp/SponGee-expressing axons. In contrast, $^{cGMP}$Sp/SponGee-Kras-expressing axons were indistinguishable from controls, demonstrating that the blockade of cGMP signaling by $^{cGMP}$Sp/SponGee in but not outside lipid rafts is sufficient to prevent slit1- and ephrinA5-induced growth cone collapse. Thus, targeting $^{cGMP}$Sp/SponGee to distinct compartments enables the control of cGMP and its downstream signaling with subcellular resolution. To investigate the limits of cGMP buffering by $^{cGMP}$Sp/SponGee, cells coexpressing $^{cGMP}$Sp/SponGee and $^T$hPDE5$^{VV}$ were exposed to longer Spermine-NONOate stimulation (two-minute pulse, or sustained exposure). Expressing SponGee was sufficient to reduce both the amplitude and delay of the FRET:CFP elevation induced by a two-minute exposure to Spermine-NONOate (FIG. 4A-C). In contrast, the cGMP elevation detected by $^T$hPDE5$^{VV}$ during a sustained Spermine-NONOate stimulation was delayed, but the peak amplitude was not affected (FIG. 4D-F), suggesting that massive and prolonged increase in cGMP concentration leads to the saturation of $^{cGMP}$Sp/SponGee cGMP binding sites in contrast to the resting concentration in this second messenger.

Figure 5:
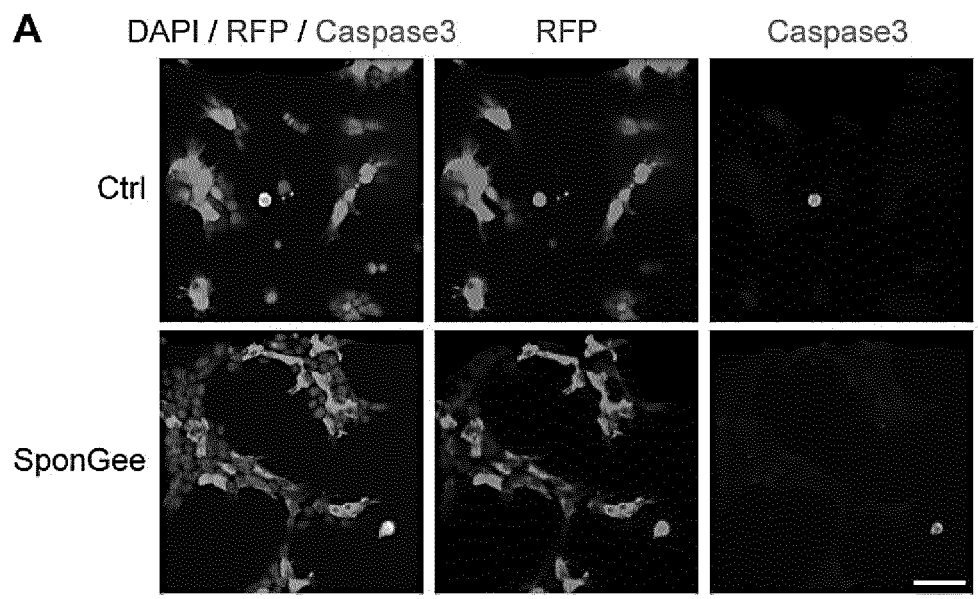
FIG. 5. SponGee does not affect cell survival. HEK293 cells were transfected with either $^{cGMP}$Sp/SponGee or RFP. Activated Caspase 3-positive cells were immunolabeled to evaluate the number of cells undergoing apoptosis. SponGee-expressing cells are not more prone to enter an apoptotic program than their RFP-expressing controls. (A) Scale bar, 50 µm (B) Data are mean±s.e.m. with individual data points, Mann-Whitney test.
Figure 5:
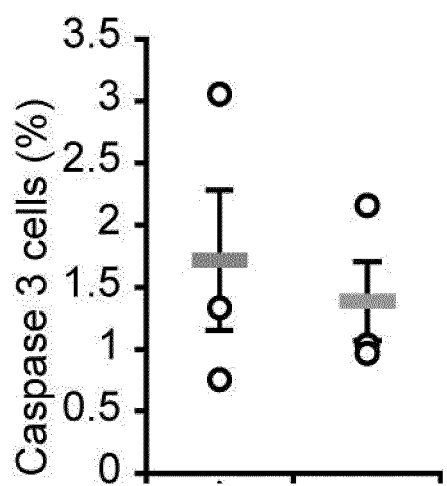

The chronic scavenging of cGMP might affect cell survival because of the role of this second messenger in many signaling pathways and cellular processes. However, the morphology of $^{cGMP}$Sp/SponGee expressing cells did not differ from their control suggesting that cell death was not affected (FIG. 5). Caspase 3 was not activated in expressing $^{cGMP}$Sp/SponGee-expressing HEK293 cells confirming that buffering cGMP with $^{cGMP}$Sp/SponGee does not affect cell survival (FIG. 5).

Figure 6:
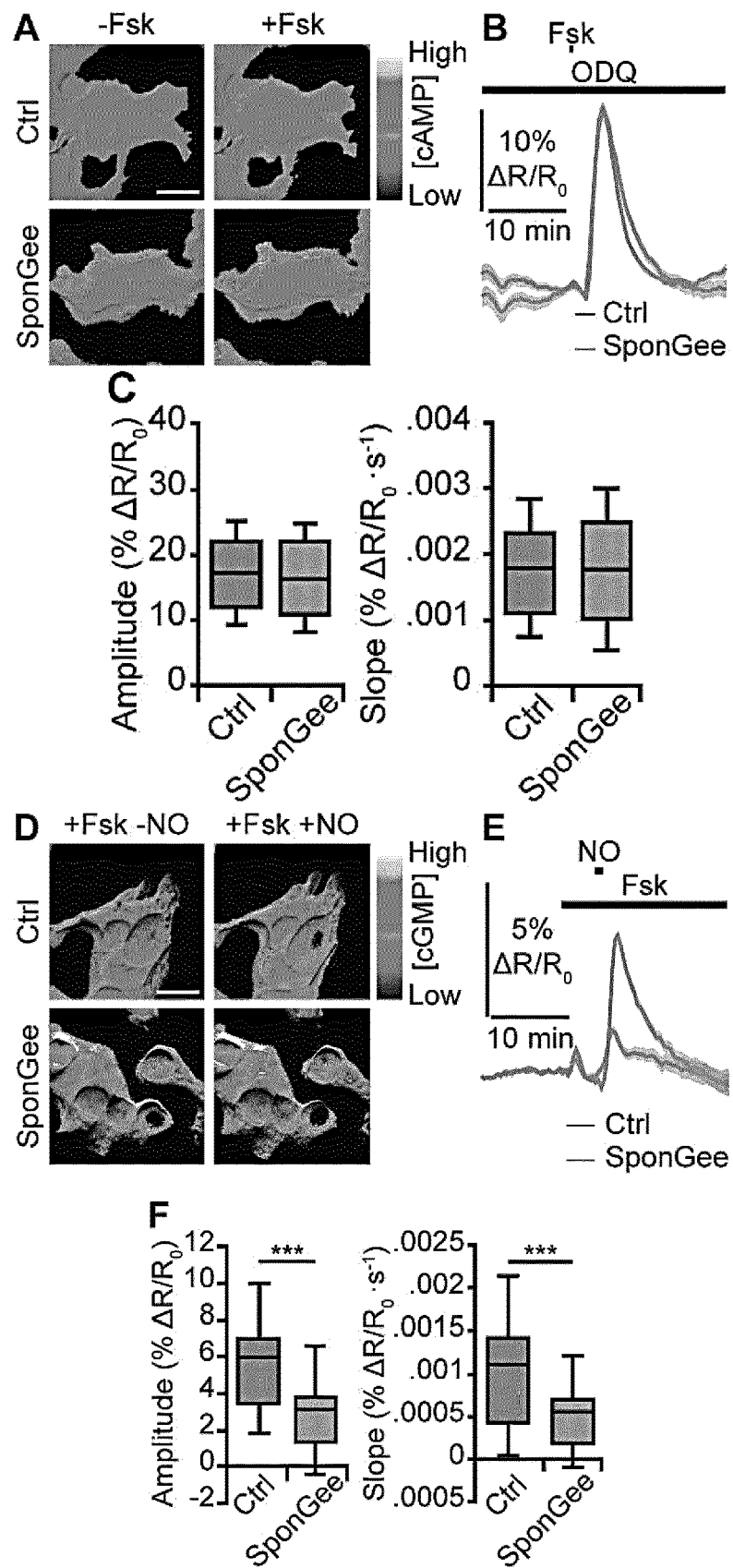
FIG. 6. SponGee is highly specific for cGMP over cAMP. (A-C) HEK293 cells were exposed to a 20-second pulse of Fsk under constant ODQ perfusion. The $^{cGMP}$Sp/SponGee-positive cells co-expressing the cAMP biosensor H147 display a similar FRET:CFP ratio amplitude and rate of increase compared to controls. (D-F) Cells were exposed to Fsk to elevate their cAMP concentration and challenge the ability of SponGee to discriminate between cGMP and cAMP. Fsk-elevated cAMP concentration did not prevent $^{cGMP}$Sp/SponGee to reduce the amplitude of the Spermine-NONOate-induced cGMP signal detected by the cGMP sensor $^{T}$hPDE5$^{VV}$. Scale bar, 20 µm. (B,E) Data are mean±s.e.m. (C,F) Box-and-whisker plot elements: center line, mean; box limits, upper and lower quartiles; whiskers, s.d.; *** P≤0.001; Mann-Whitney test.

To evaluate the specificity of $^{cGMP}$Sp/SponGee for cGMP over the closely related cAMP, FRET experiments were conducted using a cAMP bio sensor, H147. In many systems, cAMP and cGMP signaling influence each other, with the concentration of both cyclic nucleotides changing in opposite directions. To minimize the influence of cGMP scavenging by $^{cGMP}$Sp/SponGee on cAMP measurements, the cAMP buffering activity of $^{cGMP}$Sp/SponGee was evaluated in cells with pharmacologically-reduced and stabilized cGMP concentration. RFP- or $^{cGMP}$Sp/SponGee-expressing cells were maintained with reduced cGMP-signaling using the soluble guanylyl cyclase inhibitor ODQ, and later exposed to a 20 seconds pulse of the adenylyl cyclase activator Fsk. $^{cGMP}$Sp/SponGee did not reduce the amplitude or induce a delay in the elevation of cAMP concentration (FIG. 6A-C). Whether high intracellular concentrations of cAMP can bind and saturate the cGMP-binding domains of $^{cGMP}$Sp/SponGee, reducing its ability to act as a cGMP-specific scavenger, was evaluated. The buffering of NO-induced cGMP elevation by $^{cGMP}$Sp/SponGee was not affected after Fsk-induced elevation of cAMP concentrations (FIG. 6D-F), showing that cellular cAMP does not bind $^{cGMP}$Sp/SponGee, even at high concentrations. These observations demonstrate that $^{cGMP}$Sp/SponGee does not buffer intracellular cAMP and highlights its specificity for cGMP.

Figure 7:
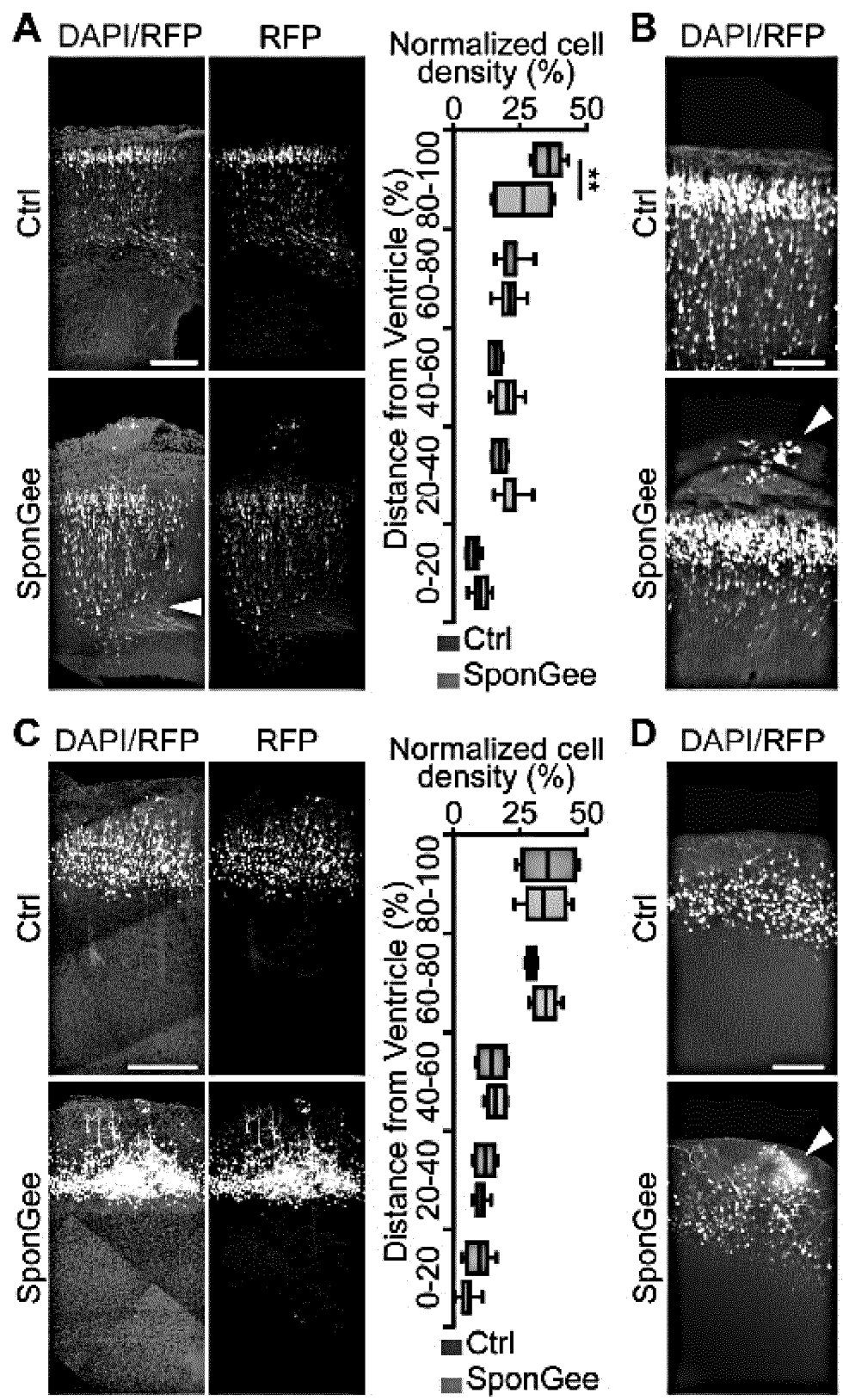
FIG. 7. SponGee alters cortical neuron migration in vivo. (A,B) Control cortical neurons electroporated at E14.5 are packed into a dense layer close to the marginal zone at E18.5. In contrast $^{cGMP}$Sp/SponGee-expression prevents the development of this layer, with (A) neurons scattered throughout the depth of the developing cortex (arrowhead), and (B) the formation of heterotopias (arrowhead) at the surface of the cortex. (C) At P10, $^{cGMP}$Sp/SponGee-electroporated neurons and their mRFP-electroporated controls are both found in the superficial layers of the cortex. (D) Heterotopias induced by $^{cGMP}$Sp/SponGee at embryonic stages are maintained in P10 pups (arrowhead), indicating that altering cGMP signaling interferes with cortical neuron migration. Box-and-whisker plot elements: center line, mean; box limits, upper and lower quartiles; whiskers, s.d. Scale bars, (A) 250 µm, (B) 100 µm, (C) 500 µm, (D) 200 µm. **P# 0.01; Two-way ANOVA and Bonferroni post hoc tests.

To evaluate the ability of $^{cGMP}$Sp/SponGee to interfere with physiological processes in vivo and thus to assess its potential as a tool to investigate cellular function in an intact organism, $^{cGMP}$Sp/SponGee was electroporated in utero in the brain lateral ventricles of E14.5 mouse embryos. The migration of electroporated cortical neurons was analyzed at E18.5 and P10. In E18.5 control eGFP and mRFP co-electroporated animals, neurons display an archetypical migration with the majority of transfected cells accumulating in the cortical plate near the marginal zone (FIG. 7A,B). In contrast, neurons co-electroporated with $^{cGMP}$Sp/SponGee and GFP exhibit a delayed migration, with neurons scattered throughout the cortical plate, including the intermediate zone (FIG. 7A). In addition, several electroporated cells failed to stall at the cortical plate, overshooting the terminal zone observed in mRFP-electroporated controls (FIG. 7B). Heterotopias were found in 7 out of 9 $^{cGMP}$Sp/SponGee-electroporated animals, whereas 2 out of 10 mRFP-expressing embryos exhibited neurons overshooting the cortical plate (P=0.000037, ₴ test). Misplaced $^{cGMP}$Sp/SponGee-expressing neurons were still found at P10 with heterotopias in 71% of the pups (5 out of 7) as compared to 20% control animals (1 out of 5, P=0.000024, ₴ test) (FIG. 7C,D). This demonstrates that cGMP buffering by $^{cGMP}$Sp/SponGee is sufficient to alter the physiological cGMP modulation required for the appropriate neuronal migration in vivo.

Figure 8:
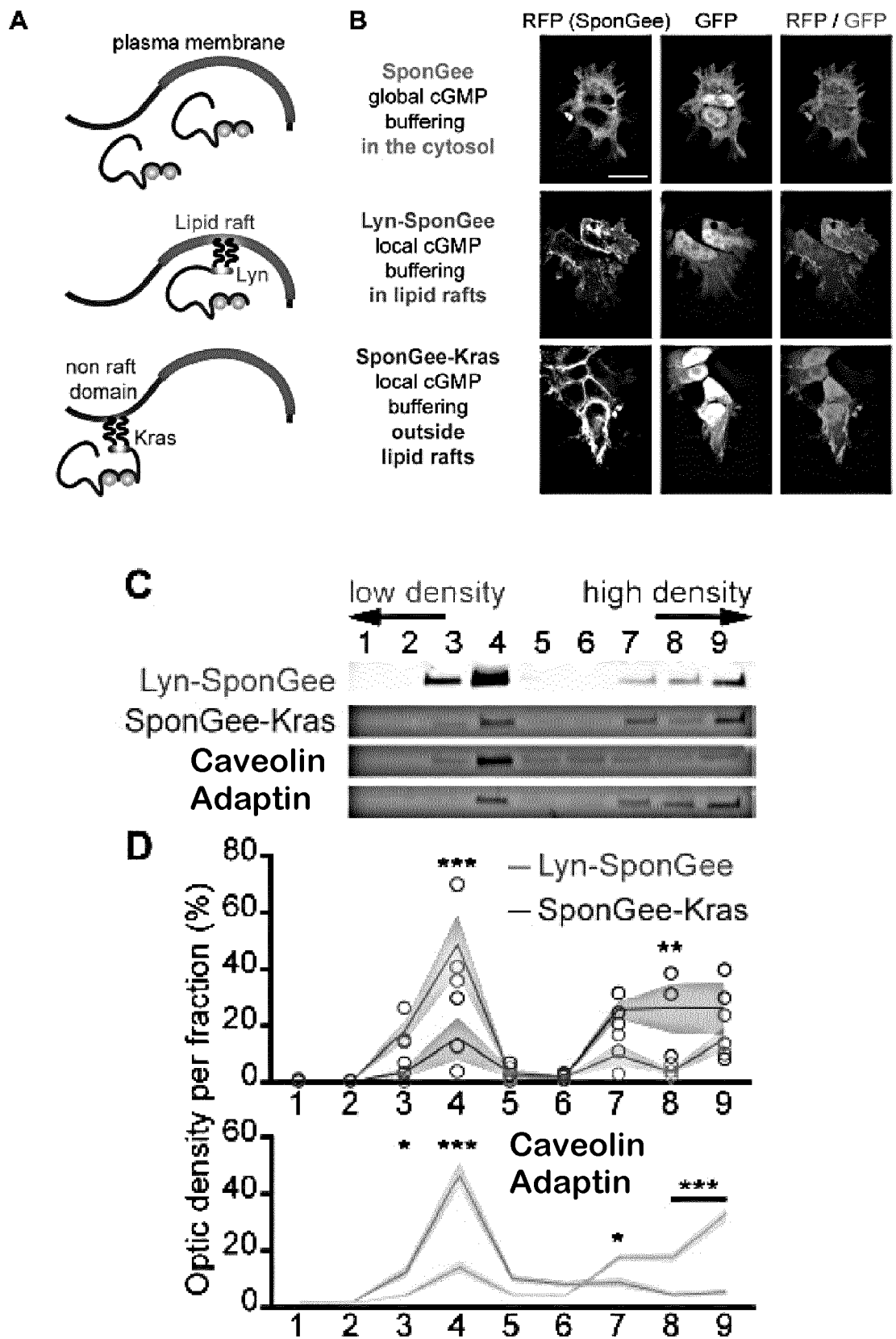
FIG. 8. Subcellular restriction of cGMP manipulation using SponGee. (A) $^{cGMP}$Sp/SponGee was either used to alter cGMP signaling in the entire cell when not targeted to any cellular compartment or to prevent the activation of cGMP downstream effectors in specific compartments. Lyn-$^{cGMP}$Sp/SponGee aims to be confined to lipid rafts whereas $^{cGMP}$Sp/SponGee e-Kras is intended to be restricted to the non-raft fraction of the plasma membrane. (B) $^{cGMP}$Sp/SponGee is detected in the cytoplasm (top row) whereas both Lyn-$^{cGMP}$Sp/SponGee and $^{cGMP}$Sp/SponGee-Kras are found at the plasma membrane (middle and bottom row). (C,D) Plasma membrane fractionation highlights distinct subcellular localization of Lyn-$^{cGMP}$Sp/SponGee and $^{cGMP}$Sp/SponGee-Kras. Lyn-$^{cGMP}$Sp/SponGee is highly enriched in fraction 4 whereas the localization of SponGee-Kras is shifted towards higher density fractions (7 to 9) (also see Figure S2). (E) Slit1 and (F) ephrinA5 induce growth cone collapse in control axons. SponGee and Lyn-SponGee prevents the collapse of growth cone. In contrast, SponGee-Kras does not affect axonal response to slit1 and ephrinA5 (also see Figures S3 and S4). Box-and-whisker plot elements: center line, mean; box limits, upper and lower quartiles; whiskers, s.d. Scale bars, (B) 20 µM, (E) 10 µm. (C,D) *P⩽0.05, P⩽0.01, *P⩽0.001; Two-way ANOVA followed by Bonferroni post hoc tests. (E,F) *P ⫫ 0.01,P⫫ 0.01, *P⫫ 0.001; Kruskal-Wallis test followed by Mann-Whitney post hoc tests.
Figure 8:
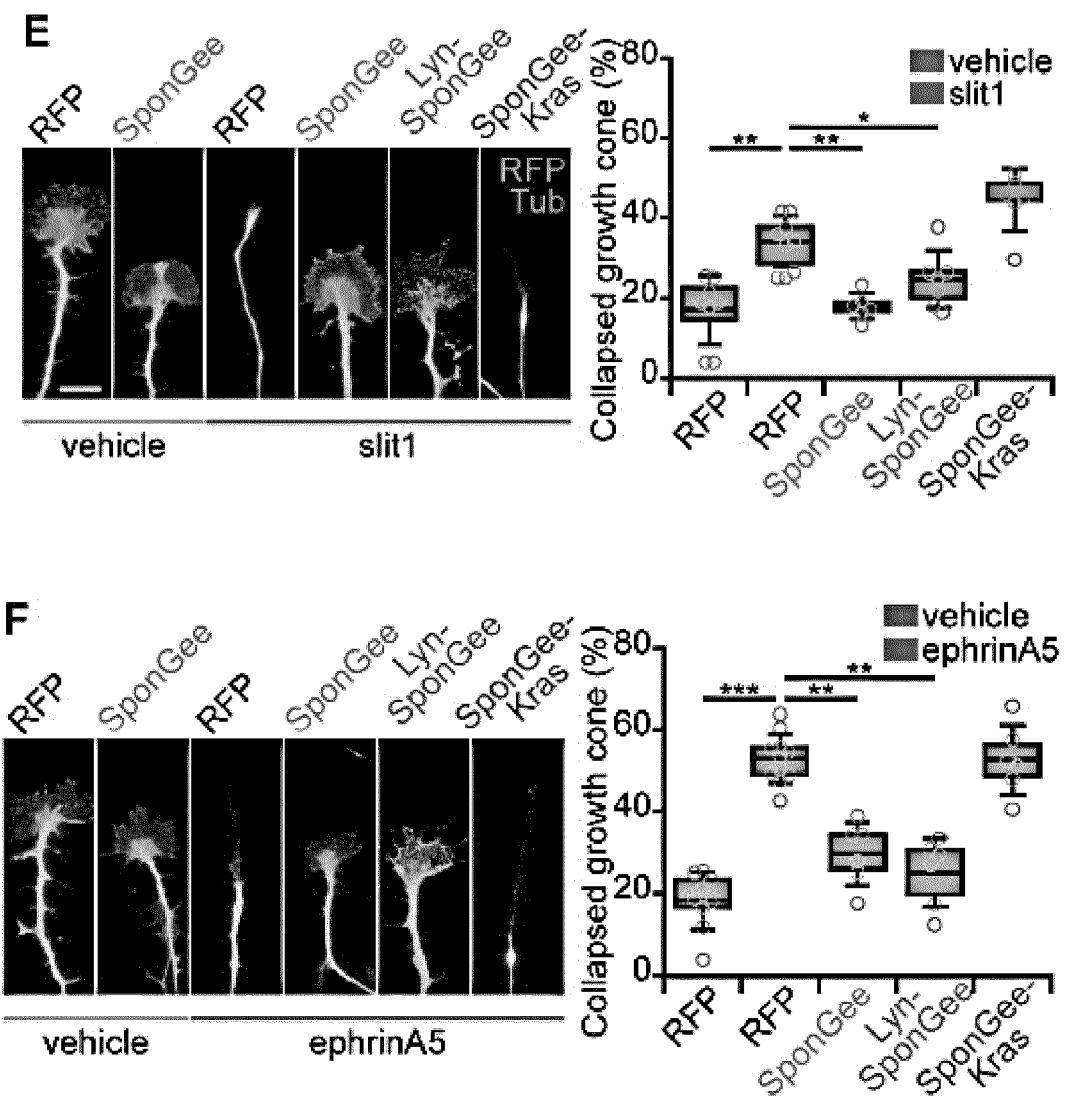

To achieve specific activation of its plethoric downstream targets, cGMP signals are confined to specific subcellular compartments. Since genetic encoding confers the ability to restrict the expression of the constructs to a specific organelle using targeting sequences, the functionality of $^{cGMP}$Sp/SponGee was assessed in this scenario. We targeted the cGMP buffer to the membrane, further restricting its expression to the lipid raft microdomains by the N-terminal fusion of a tandem of palmitoylation-myristoylation targeting peptides from Lyn Kinase (Lyn-$^{cGMP}$Sp/SponGee), or excluding it from the lipid raft domain by the C-terminal fusion of a CaaX-polylysine motif derived from K-Ras ($^{cGMP}$Sp/SponGee-Kras) (FIG. 8A). Lyn-$^{cGMP}$Sp/SponGee and $^{cGMP}$Sp/SponGee-Kras expression was restricted to the membrane, in contrast to the untargeted $^{cGMP}$Sp/SponGee (FIG. 8B). We analyzed the localization of Lyn-$^{cGMP}$Sp/SponGee and $^{cGMP}$Sp/SponGee-Kras in distinct membrane compartments using membrane fractionation in a density gradient. Lyn-$^{cGMP}$Sp/SponGee expression was restricted to low-density fractions, concomitant with the lipid raft marker Caveolin. In contrast, $^{cGMP}$Sp/SponGee-Kras was enriched in the high-density fractions together with ϕ-Adaptin, a marker of the non-raft component of the membrane (FIG. 8C,D). To assess whether compartmentalization of $^{cGMP}$Sp/SponGee differentially affects cGMP-dependent cellular responses, the behavior of retinal ganglion cell growth cones expressing either Lyn-$^{cGMP}$Sp/SponGee or $^{cGMP}$Sp/SponGee-Kras when exposed to the axon guidance molecules slit1 and ephrinA5 were analyzed. Slit1- and ephrinA5-dependent repulsion of axonal growth cones require cGMP signaling. In control conditions, including untransfected axons and mRFP-electroporated axons, slit1 and ephrinA5 induced the collapse of the growth cone (FIG. 8E,F). $^{cGMP}$Sp/SponGee expression in the cytosol abolished the collapse response induced by both cues, confirming the requirement of cGMP signaling in this process. Similarly, slit1 and ephrinA5 failed to induce growth cone collapse in Lyn-$^{cGMP}$Sp/SponGee-expressing axons. In contrast, $^{cGMP}$Sp/SponGee-Kras-expressing axons were indistinguishable from controls (FIG. 8E,F), demonstrating that the blockade of cGMP signaling by $^{cGMP}$Sp/SponGee in but not outside lipid rafts is sufficient to prevent slit1- and ephrinA5-induced growth cone collapse. Thus, targeting $^{cGMP}$Sp/SponGee to distinct compartments enables the control of cGMP and its downstream signaling with subcellular resolution. In conclusion, the polypeptide of the invention functions as a cGMP scavenger able to interfere with physiological functions that rely on this second messenger. The polypeptide of the invention, can therefore alter cGMP responses in a cell-specific manner and with subcellular resolution, opening new fields for the precise study of signaling cascades and paving the way for therapeutic implementation.

The invention claimed is:

1. A polypeptide comprising:
a chimeric peptide comprising at least a sequence corresponding to SEQ ID NO: 1 or a fragment thereof, and at least a sequence corresponding to SEQ ID NO: 2 or a fragment thereof;
a cGMP binding domain comprising the sequence as set forth in SEQ ID NO: 6; and,
wherein said polypeptide is devoid of any catalytic domain,
and its functional variants that bind cGMP and have a sequence with at least 80% identity with the sequence of said polypeptide and which derives from the sequence of said polypeptide by conservative substitutions.

2. The polypeptide of claim 1, wherein the chimeric peptide comprises the sequence as set forth in SEQ ID NO: 3, 4 or 5.

3. The polypeptide of claim 1, wherein the cGMP binding domain comprises the sequence as set forth in SEQ ID NO: 7 or the sequence as set forth in SEQ ID NO: 8.

4. The polypeptide of claim 1, wherein the cGMP binding domain comprises the sequence as set forth in SEQ ID NO: 9 or the sequence as set forth in SEQ ID NO: 10.

5. The polypeptide of claim 1, wherein the chimeric peptide and the cGMP binding domain form a contiguous sequence.

6. The polypeptide of claim 1, wherein the polypeptide comprises a peptide signal.

7. The polypeptide of claim 6, wherein the peptide signal which comprises tandem repeats of the sequence as set forth in SEQ ID NO: 7.

8. The polypeptide of claim 1, wherein the polypeptide comprises a fluorescent peptide.

9. The polypeptide of claim 2, wherein the chimeric peptide comprises the sequence as set forth in SEQ ID NO: 3.

10. The polypeptide of claim 5, wherein a C-terminal end of the chimeric peptide is fused to a N-terminal end of the cGMP binding domain.

11. The polypeptide of claim 8, wherein the fluorescent peptide is selected from the group consisting of green fluorescent protein (GFP), cyan fluorescent protein (CFP), yellow fluorescent protein (YFP), red fluorescent protein (RFP), and variants thereof.

* * * * *

SEQUENCE LISTING

```
<160> NUMBER OF SEQ ID NOS: 17

<210> SEQ ID NO 1
<211> LENGTH: 89
<212> TYPE: PRT
<213> ORGANISM: bos taurus

<400> SEQUENCE: 1

Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
            20                  25                  30

Ile Gln Glu Leu Lys Arg Lys Leu His Lys Cys Gln Ser Val Leu Pro
        35                  40                  45

Val Pro Ser Thr His Ile Gly Pro Arg Thr Thr Arg Ala Gln Gly Ile
    50                  55                  60

Ser Ala Glu Pro Gln Thr Tyr Arg Ser Phe His Asp Leu Arg Gln Ala
65                  70                  75                  80

Phe Arg Lys Phe Thr Lys Ser Glu Arg
                85
```

<210> SEQ ID NO 2
<211> LENGTH: 104
<212> TYPE: PRT
<213> ORGANISM: bos taurus

<400> SEQUENCE: 2

Met Gly Thr Leu Arg Asp Leu Gln Tyr Ala Leu Gln Glu Lys Ile Glu
1               5                   10                  15

Glu Leu Arg Gln Arg Asp Ala Leu Ile Asp Glu Leu Glu Leu Glu Leu
            20                  25                  30

Asp Gln Lys Asp Glu Leu Ile Gln Lys Leu Gln Asn Glu Leu Asp Lys
        35                  40                  45

Tyr Arg Ser Val Ile Arg Pro Ala Thr Gln Gln Ala Gln Lys Gln Ser
    50                  55                  60

Ala Ser Thr Leu Gln Gly Glu Pro Arg Thr Lys Arg Gln Ala Ile Ser
65                  70                  75                  80

Ala Glu Pro Thr Ala Phe Asp Ile Gln Asp Leu Ser His Val Thr Leu
                85                  90                  95

Pro Phe Tyr Pro Lys Ser Pro Gln
            100

<210> SEQ ID NO 3
<211> LENGTH: 89
<212> TYPE: PRT
<213> ORGANISM: artificial
<220> FEATURE:
<223> OTHER INFORMATION: residues 1-78 of bovine PKG Ia fused to
      residues 94 to 104 of bovine PKG Ib

<400> SEQUENCE: 3

Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
            20                  25                  30

Ile Gln Glu Leu Lys Arg Lys Leu His Lys Cys Gln Ser Val Leu Pro
        35                  40                  45

Val Pro Ser Thr His Ile Gly Pro Arg Thr Thr Arg Ala Gln Gly Ile
    50                  55                  60

Ser Ala Glu Pro Gln Thr Tyr Arg Ser Phe His Asp Leu Arg Val Thr
65                  70                  75                  80

Leu Pro Phe Tyr Pro Lys Ser Pro Gln
                85

<210> SEQ ID NO 4
<211> LENGTH: 104
<212> TYPE: PRT
<213> ORGANISM: artificial
<220> FEATURE:
<223> OTHER INFORMATION: residues 1-65 of bovine PKG Ib, fused to
      residues 51-78 of bovine PKG Ia, fused to residues 94 to 104 of
      bovine PKG Ib

<400> SEQUENCE: 4

Met Gly Thr Leu Arg Asp Leu Gln Tyr Ala Leu Gln Glu Lys Ile Glu
1               5                   10                  15

Glu Leu Arg Gln Arg Asp Ala Leu Ile Asp Glu Leu Glu Leu Glu Leu
            20                  25                  30

Asp Gln Lys Asp Glu Leu Ile Gln Lys Leu Gln Asn Glu Leu Asp Lys
        35                  40                  45

Tyr Arg Ser Val Ile Arg Pro Ala Thr Gln Gln Ala Gln Lys Gln Ser

```
                    50                  55                  60

Ala Ser Thr His Ile Gly Pro Arg Thr Thr Arg Ala Gln Gly Ile Ser
 65                  70                  75                  80

Ala Glu Pro Gln Thr Tyr Arg Ser Phe His Asp Leu Arg Val Thr Leu
                     85                  90                  95

Pro Phe Tyr Pro Lys Ser Pro Gln
                100
```

<210> SEQ ID NO 5
<211> LENGTH: 89
<212> TYPE: PRT
<213> ORGANISM: artificial
<220> FEATURE:
<223> OTHER INFORMATION: residues 1-50 of bovine PKG Ia, fused to
      residues 66-83 of bovine PKG Ib, fused to residues 69-78 of bovine
      PKG Ia, fused to residues 94 to 104 of bovine PKG Ib

<400> SEQUENCE: 5

```
Met Ser Glu Leu Glu Glu Asp Phe Ala Lys Ile Leu Met Leu Lys Glu
 1               5                  10                  15

Glu Arg Ile Lys Glu Leu Glu Lys Arg Leu Ser Glu Lys Glu Glu Glu
                20                  25                  30

Ile Gln Glu Leu Lys Arg Lys Leu His Lys Cys Gln Ser Val Leu Pro
                35                  40                  45

Val Pro Ser Thr Leu Gln Gly Glu Pro Arg Thr Lys Arg Gln Ala Ile
 50                  55                  60

Ser Ala Glu Pro Gln Thr Tyr Arg Ser Phe His Asp Leu Arg Val Thr
 65                  70                  75                  80

Leu Pro Phe Tyr Pro Lys Ser Pro Gln
                85
```

<210> SEQ ID NO 6
<211> LENGTH: 247
<212> TYPE: PRT
<213> ORGANISM: artificial
<220> FEATURE:
<223> OTHER INFORMATION: cGMP binding domain consensus sequence
<220> FEATURE:
<221> NAME/KEY: misc_feature
<222> LOCATION: (1)..(247)
<223> OTHER INFORMATION: Any amino-acid residue
<220> FEATURE:
<221> NAME/KEY: misc_feature
<222> LOCATION: (1)..(247)
<223> OTHER INFORMATION: Xaa is any amino-acid residue

<400> SEQUENCE: 6

```
Phe Xaa Lys Xaa Leu Xaa Xaa Gln Ile Xaa Xaa Xaa Val Xaa Cys Met
 1               5                  10                  15

Tyr Xaa Xaa Xaa Tyr Xaa Xaa Xaa Ser Xaa Ile Ile Lys Xaa Gly Xaa
                20                  25                  30

Xaa Gly Xaa Xaa Xaa Xaa Val Xaa Xaa Xaa Gly Xaa Xaa Glu Val Xaa
            35                  40                  45

Xaa Xaa Xaa Xaa Xaa Leu Xaa Xaa Xaa Xaa Xaa Xaa Xaa Xaa Phe Gly
 50                  55                  60

Glu Leu Ala Ile Leu Tyr Asn Cys Thr Arg Thr Ala Xaa Val Lys Xaa
 65                  70                  75                  80

Xaa Xaa Asn Val Lys Xaa Trp Ala Xaa Asp Arg Xaa Xaa Phe Gln Xaa
                85                  90                  95

Ile Met Xaa Arg Thr Xaa Xaa Xaa Xaa Xaa Xaa Xaa Tyr Xaa Xaa Phe
                100                 105                 110
```

```
Leu Xaa Ser Xaa Xaa Xaa Xaa Xaa Leu Pro Glu Xaa Xaa Leu Xaa
    115                 120                 125

Lys Xaa Xaa Asp Xaa Leu Glu Xaa Xaa Xaa Tyr Xaa Xaa Gly Xaa Tyr
    130                 135                 140

Ile Ile Arg Xaa Gly Xaa Xaa Gly Xaa Thr Phe Phe Ile Xaa Xaa Lys
145                 150                 155                 160

Gly Xaa Val Xaa Val Thr Xaa Xaa Xaa Xaa Xaa Xaa Xaa Pro Xaa
                165                 170                 175

Xaa Xaa Xaa Thr Leu Xaa Lys Gly Xaa Xaa Phe Gly Glu Lys Ala Leu
            180                 185                 190

Xaa Xaa Xaa Asp Val Arg Xaa Ala Asn Xaa Ile Ala Xaa Glu Xaa Xaa
            195                 200                 205

Val Xaa Cys Leu Val Ile Asp Arg Xaa Xaa Phe Xaa Xaa Xaa Xaa Gly
    210                 215                 220

Xaa Xaa Xaa Xaa Xaa Xaa Xaa Xaa Xaa Xaa Xaa Val Xaa Asn Xaa
225                 230                 235                 240

Xaa Xaa Xaa Asp Xaa Xaa Xaa
            245

<210> SEQ ID NO 7
<211> LENGTH: 239
<212> TYPE: PRT
<213> ORGANISM: homo sapiens

<400> SEQUENCE: 7

Phe Met Lys Asn Leu Glu Leu Ser Gln Ile Gln Glu Ile Val Asp Cys
1               5                   10                  15

Met Tyr Pro Val Glu Tyr Gly Lys Asp Ser Cys Ile Ile Lys Glu Gly
                20                  25                  30

Asp Val Gly Ser Leu Val Tyr Val Met Glu Asp Gly Lys Val Glu Val
            35                  40                  45

Thr Lys Glu Gly Val Lys Leu Cys Thr Met Gly Pro Gly Lys Val Phe
50                  55                  60

Gly Glu Leu Ala Ile Leu Tyr Asn Cys Thr Arg Thr Ala Thr Val Lys
65                  70                  75                  80

Thr Leu Val Asn Val Lys Leu Trp Ala Ile Asp Arg Gln Cys Phe Gln
                85                  90                  95

Thr Ile Met Met Arg Thr Gly Leu Ile Lys His Thr Glu Tyr Met Glu
            100                 105                 110

Phe Leu Lys Ser Val Pro Thr Phe Gln Ser Leu Pro Glu Glu Ile Leu
        115                 120                 125

Ser Lys Leu Ala Asp Val Leu Glu Glu Thr His Tyr Glu Asn Gly Glu
    130                 135                 140

Tyr Ile Ile Arg Gln Gly Ala Arg Gly Asp Thr Phe Phe Ile Ile Ser
145                 150                 155                 160

Lys Gly Thr Val Asn Val Thr Arg Glu Asp Ser Pro Ser Glu Asp Pro
                165                 170                 175

Val Phe Leu Arg Thr Leu Gly Lys Gly Asp Trp Phe Gly Glu Lys Ala
            180                 185                 190

Leu Gln Gly Glu Asp Val Arg Thr Ala Asn Val Ile Ala Ala Glu Ala
        195                 200                 205

Val Thr Cys Leu Val Ile Asp Arg Asp Ser Phe Lys His Leu Ile Gly
    210                 215                 220

Gly Leu Asp Asp Val Ser Asn Lys Ala Tyr Glu Asp Ala Glu Ala
```

<210> SEQ ID NO 8
<211> LENGTH: 309
<212> TYPE: PRT
<213> ORGANISM: homo sapiens

<400> SEQUENCE: 8

Phe Leu Lys Arg Leu Asp Pro Gln Gln Ile Lys Asp Met Val Glu Cys
1               5                   10                  15

Met Tyr Gly Arg Asn Tyr Gln Gln Gly Ser Tyr Ile Ile Lys Gln Gly
            20                  25                  30

Glu Pro Gly Asn His Ile Phe Val Leu Ala Glu Gly Arg Leu Glu Val
        35                  40                  45

Phe Gln Gly Glu Lys Leu Leu Ser Ser Ile Pro Met Trp Thr Thr Phe
    50                  55                  60

Gly Glu Leu Ala Ile Leu Tyr Asn Cys Thr Arg Thr Ala Ser Val Lys
65                  70                  75                  80

Ala Ile Thr Asn Val Lys Thr Trp Ala Leu Asp Arg Glu Val Phe Gln
                85                  90                  95

Asn Ile Met Arg Arg Thr Ala Gln Ala Arg Asp Glu Gly Tyr Arg Asn
            100                 105                 110

Phe Leu Arg Ser Val Ser Leu Leu Lys Asn Leu Pro Glu Asp Lys Leu
        115                 120                 125

Thr Lys Ile Ile Asp Cys Leu Glu Val Glu Tyr Tyr Asp Lys Gly Asp
    130                 135                 140

Tyr Ile Ile Arg Glu Gly Glu Gly Gly Ser Thr Phe Phe Ile Leu Ala
145                 150                 155                 160

Lys Gly Lys Val Lys Val Thr Gln Ser Thr Glu Gly His Asp Gln Pro
                165                 170                 175

Gln Leu Ile Lys Thr Leu Gln Lys Gly Glu Tyr Phe Gly Glu Lys Ala
            180                 185                 190

Leu Cys Leu Glu Val Glu Tyr Tyr Asp Lys Gly Asp Tyr Ile Ile Arg
        195                 200                 205

Glu Gly Glu Glu Gly Ser Thr Phe Phe Ile Leu Ala Lys Gly Lys Val
    210                 215                 220

Lys Val Thr Gln Ser Thr Glu Gly His Asp Gln Pro Gln Leu Ile Lys
225                 230                 235                 240

Thr Leu Gln Lys Gly Glu Tyr Phe Gly Glu Lys Ala Leu Ile Ser Asp
                245                 250                 255

Asp Val Arg Ser Ala Asn Ile Ile Ala Glu Glu Asn Asp Val Ala Cys
            260                 265                 270

Leu Val Ile Asp Arg Glu Thr Phe Asn Gln Thr Val Gly Thr Phe Glu
        275                 280                 285

Glu Leu Gln Lys Tyr Leu Glu Gly Tyr Val Ala Asn Leu Asn Arg Asp
    290                 295                 300

Asp Glu Lys Arg His
305

<210> SEQ ID NO 9
<211> LENGTH: 267
<212> TYPE: PRT
<213> ORGANISM: homo sapiens

<400> SEQUENCE: 9

Ser Lys Asp Leu Ile Lys Glu Ala Ile Leu Asp Asn Asp Phe Met Lys

```
1               5                   10                  15
Asn Leu Glu Leu Ser Gln Ile Gln Glu Ile Val Asp Cys Met Tyr Pro
            20                  25                  30

Val Glu Tyr Gly Lys Asp Ser Cys Ile Ile Lys Glu Gly Asp Val Gly
            35                  40                  45

Ser Leu Val Tyr Val Met Glu Asp Gly Lys Val Glu Val Thr Lys Glu
            50                  55                  60

Gly Val Lys Leu Cys Thr Met Gly Pro Gly Lys Val Phe Gly Glu Leu
65                  70                  75                  80

Ala Ile Leu Tyr Asn Cys Thr Arg Thr Ala Thr Val Lys Thr Leu Val
                85                  90                  95

Asn Val Lys Leu Trp Ala Ile Asp Arg Gln Cys Phe Gln Thr Ile Met
            100                 105                 110

Met Arg Thr Gly Leu Ile Lys His Thr Glu Tyr Met Glu Phe Leu Lys
            115                 120                 125

Ser Val Pro Thr Phe Gln Ser Leu Pro Glu Glu Ile Leu Ser Lys Leu
            130                 135                 140

Ala Asp Val Leu Glu Glu Thr His Tyr Glu Asn Gly Glu Tyr Ile Ile
145                 150                 155                 160

Arg Gln Gly Ala Arg Gly Asp Thr Phe Phe Ile Ile Ser Lys Gly Thr
                165                 170                 175

Val Asn Val Thr Arg Glu Asp Ser Pro Ser Glu Asp Pro Val Phe Leu
            180                 185                 190

Arg Thr Leu Gly Lys Gly Asp Trp Phe Gly Glu Lys Ala Leu Gln Gly
            195                 200                 205

Glu Asp Val Arg Thr Ala Asn Val Ile Ala Ala Glu Ala Val Thr Cys
            210                 215                 220

Leu Val Ile Asp Arg Asp Ser Phe Lys His Leu Ile Gly Gly Leu Asp
225                 230                 235                 240

Asp Val Ser Asn Lys Ala Tyr Glu Asp Ala Glu Ala Lys Ala Asp Pro
                245                 250                 255

Cys Thr Tyr Pro Tyr Asp Val Pro Asp Tyr Ala
            260                 265

<210> SEQ ID NO 10
<211> LENGTH: 268
<212> TYPE: PRT
<213> ORGANISM: bos taurus

<400> SEQUENCE: 10

Ser Lys Ile Asp Leu Ile Lys Glu Ala Ile Leu Asp Asn Asp Phe Met
1               5                   10                  15

Lys Asn Leu Glu Leu Ser Gln Ile Gln Glu Ile Val Asp Cys Met Tyr
            20                  25                  30

Pro Val Glu Tyr Gly Lys Asp Ser Cys Ile Ile Lys Glu Gly Asp Val
            35                  40                  45

Gly Ser Leu Val Tyr Val Met Glu Asp Gly Lys Val Glu Val Thr Lys
            50                  55                  60

Glu Gly Val Lys Leu Cys Thr Met Gly Pro Gly Lys Val Phe Gly Glu
65                  70                  75                  80

Leu Ala Ile Leu Tyr Asn Cys Thr Arg Thr Ala Thr Val Lys Thr Leu
                85                  90                  95

Val Asn Val Lys Leu Trp Ala Ile Asp Arg Gln Cys Phe Gln Thr Ile
            100                 105                 110
```

Met Met Arg Thr Gly Leu Ile Lys His Thr Glu Tyr Met Glu Phe Leu
            115                 120                 125

Lys Ser Val Pro Thr Phe Gln Ser Leu Pro Glu Glu Ile Leu Ser Lys
        130                 135                 140

Leu Ala Asp Val Leu Glu Glu Thr His Tyr Glu Asn Gly Glu Tyr Ile
145                 150                 155                 160

Ile Arg Gln Gly Ala Arg Gly Asp Thr Phe Phe Ile Ile Ser Lys Gly
                165                 170                 175

Thr Val Asn Val Thr Arg Glu Asp Ser Pro Ser Glu Asp Pro Val Phe
            180                 185                 190

Leu Arg Thr Leu Gly Lys Gly Asp Trp Phe Gly Glu Lys Ala Leu Gln
        195                 200                 205

Gly Glu Asp Val Arg Thr Ala Asn Val Ile Ala Ala Glu Ala Val Thr
210                 215                 220

Cys Leu Val Ile Asp Arg Asp Ser Phe Lys His Leu Ile Gly Gly Leu
225                 230                 235                 240

Asp Asp Val Ser Asn Lys Ala Tyr Glu Asp Ala Glu Ala Lys Ala Asp
                245                 250                 255

Pro Cys Thr Tyr Pro Tyr Asp Val Pro Asp Tyr Ala
            260                 265

<210> SEQ ID NO 11
<211> LENGTH: 267
<212> TYPE: PRT
<213> ORGANISM: bos taurus

<400> SEQUENCE: 11

Phe Asn Ile Ile Asp Thr Leu Gly Val Gly Gly Phe Gly Arg Val Glu
1               5                   10                  15

Leu Val Gln Leu Lys Ser Glu Glu Ser Lys Thr Phe Ala Met Lys Ile
            20                  25                  30

Leu Lys Lys Arg His Ile Val Asp Thr Arg Gln Gln Glu His Ile Arg
        35                  40                  45

Ser Glu Lys Gln Ile Met Gln Gly Ala His Ser Asp Phe Ile Val Arg
    50                  55                  60

Leu Tyr Arg Thr Phe Lys Asp Ser Lys Tyr Leu Tyr Met Leu Met Glu
65                  70                  75                  80

Ala Cys Leu Gly Gly Glu Leu Trp Thr Ile Leu Arg Asp Arg Gly Ser
                85                  90                  95

Phe Glu Asp Ser Thr Thr Arg Phe Tyr Thr Ala Cys Val Val Glu Ala
            100                 105                 110

Phe Ala Tyr Leu His Ser Lys Gly Ile Ile Tyr Arg Asp Leu Lys Pro
        115                 120                 125

Glu Asn Leu Ile Leu Asp His Arg Gly Tyr Ala Lys Leu Val Asp Phe
    130                 135                 140

Gly Phe Ala Lys Lys Ile Gly Phe Gly Lys Lys Thr Trp Thr Phe Cys
145                 150                 155                 160

Gly Thr Pro Glu Tyr Val Ala Pro Glu Ile Ile Leu Asn Lys Gly His
                165                 170                 175

Asp Ile Ser Ala Asp Tyr Trp Ser Leu Gly Ile Leu Met Tyr Glu Leu
            180                 185                 190

Leu Thr Gly Ser Pro Pro Phe Ser Gly Pro Asp Pro Met Lys Thr Tyr
        195                 200                 205

Asn Ile Ile Leu Arg Gly Ile Asp Met Ile Glu Phe Pro Lys Lys Ile
    210                 215                 220

Ala Lys Asn Ala Ala Asn Leu Ile Lys Lys Leu Cys Arg Asp Asn Pro
225                 230                 235                 240

Ser Glu Arg Leu Gly Asn Leu Lys Asn Gly Val Lys Asp Ile Gln Lys
                245                 250                 255

His Lys Trp Phe Glu Gly Phe Asn Trp Glu Gly
            260                 265

<210> SEQ ID NO 12
<211> LENGTH: 267
<212> TYPE: PRT
<213> ORGANISM: bos taurus

<400> SEQUENCE: 12

Phe Asn Ile Ile Asp Thr Leu Gly Val Gly Gly Phe Gly Arg Val Glu
1               5                   10                  15

Leu Val Gln Leu Lys Ser Glu Ser Lys Thr Phe Ala Met Lys Ile
                20                  25                  30

Leu Lys Lys Arg His Ile Val Asp Thr Arg Gln Gln Glu His Ile Arg
            35                  40                  45

Ser Glu Lys Gln Ile Met Gln Gly Ala His Ser Asp Phe Ile Val Arg
50                  55                  60

Leu Tyr Arg Thr Phe Lys Asp Ser Lys Tyr Leu Tyr Met Leu Met Glu
65                  70                  75                  80

Ala Cys Leu Gly Gly Glu Leu Trp Thr Ile Leu Arg Asp Arg Gly Ser
                85                  90                  95

Phe Glu Asp Ser Thr Thr Arg Phe Tyr Thr Ala Cys Val Val Glu Ala
            100                 105                 110

Phe Ala Tyr Leu His Ser Lys Gly Ile Ile Tyr Arg Asp Leu Lys Pro
        115                 120                 125

Glu Asn Leu Ile Leu Asp His Arg Gly Tyr Ala Lys Leu Val Asp Phe
130                 135                 140

Gly Phe Ala Lys Lys Ile Gly Phe Gly Lys Lys Thr Trp Thr Phe Cys
145                 150                 155                 160

Gly Thr Pro Glu Tyr Val Ala Pro Glu Ile Ile Leu Asn Lys Gly His
                165                 170                 175

Asp Ile Ser Ala Asp Tyr Trp Ser Leu Gly Ile Leu Met Tyr Glu Leu
            180                 185                 190

Leu Thr Gly Ser Pro Pro Phe Ser Gly Pro Asp Pro Met Lys Thr Tyr
        195                 200                 205

Asn Ile Ile Leu Arg Gly Ile Asp Met Ile Glu Phe Pro Lys Lys Ile
210                 215                 220

Ala Lys Asn Ala Ala Asn Leu Ile Lys Lys Leu Cys Arg Asp Asn Pro
225                 230                 235                 240

Ser Glu Arg Leu Gly Asn Leu Lys Asn Gly Val Lys Asp Ile Gln Lys
                245                 250                 255

His Lys Trp Phe Glu Gly Phe Asn Trp Glu Gly
            260                 265

<210> SEQ ID NO 13
<211> LENGTH: 22
<212> TYPE: PRT
<213> ORGANISM: artificial
<220> FEATURE:
<223> OTHER INFORMATION: Lyn Kinase N-terminus fragment

<400> SEQUENCE: 13

Met Gly Cys Ile Lys Ser Lys Arg Lys Asp Lys Met Gly Cys Ile Lys
1               5                   10                  15

Ser Lys Arg Lys Asp Lys
            20

<210> SEQ ID NO 14
<211> LENGTH: 14
<212> TYPE: PRT
<213> ORGANISM: artificial
<220> FEATURE:
<223> OTHER INFORMATION: CaaX-polylysine motif of Kras

<400> SEQUENCE: 14

Lys Lys Lys Lys Lys Lys Ser Lys Thr Lys Cys Val Ile Met
1               5                   10

<210> SEQ ID NO 15
<211> LENGTH: 1028
<212> TYPE: DNA
<213> ORGANISM: artificial
<220> FEATURE:
<223> OTHER INFORMATION: full artificial construct

<400> SEQUENCE: 15

| | | |
|---|---|---|
| atgagcgagc tggaggaaga ctttgccaag attctcatgc tcaaggagga gaggatcaaa | 60 |
| gagctggaga gcggctgtc agagaaggag gaagaaatcc aggagctgaa gaggaaactc | 120 |
| cataaatgcc agtcagtgct gcccgtgccc tcgacccaca tcggccccg gaccacccgg | 180 |
| gcacagggca tctcggccga gccgcagacc tacaggtcct ccacgacct ccgagtgacc | 240 |
| ctgcccttct accccaagag tccacagtcc aagatcgatc tcataaagga ggccatcctt | 300 |
| gacaatgact ttatgaagaa cttggagctg tcacagatcc aagagattgt ggattgtatg | 360 |
| tacccagtgg agtacggcaa agacagctgc atcatcaaag aaggagatgt ggggtcactg | 420 |
| gtgtatgtca tggaagatgg taaggttgaa gttacaaaag aaggcgtgaa gctgtgcaca | 480 |
| atgggtcctg gtaaagtgtt tggagagttg gctatccttt acaactgtac ccggacggcg | 540 |
| accgtcaaaa ctcttgtaaa tgtgaaactc tgggccattg atcgacaatg ttttcagacg | 600 |
| ataatgatga ggacaggact tatcaagcat accgagtata tggaattttt aaaaagcgtt | 660 |
| ccaacattcc agagccttcc tgaagagatc ctcagtaaac ttgctgacgt ccttgaagag | 720 |
| acccactatg aaaatgggga atatatcatc aggcaaggtg caagagggga caccttcttt | 780 |
| atcatcagta aggaaaggt taatgtcact cgtgaagact cgcccaatga agacccagtc | 840 |
| tttcttagaa ccttaggaaa aggagattgg tttggagaga agccttgca ggggaagat | 900 |
| gtgagaacag cgaatgtaat tgcggcagaa gctgtaacct gccttgtgat cgacagagac | 960 |
| tctttcaaac atttgattgg aggattagat gatgtttcta aaaagcatat gaagatgcag | 1020 |
| aagctaag | 1028 |

<210> SEQ ID NO 16
<211> LENGTH: 66
<212> TYPE: DNA
<213> ORGANISM: artificial
<220> FEATURE:
<223> OTHER INFORMATION: Lyn Kinase N-terminus construct

<400> SEQUENCE: 16

| | | |
|---|---|---|
| atgggctgca tcaagagcaa gcgcaaggac aagatgggct gcatcaagag caagcgcaag | 60 |
| gacaag | 66 |

```
<210> SEQ ID NO 17
<211> LENGTH: 45
<212> TYPE: DNA
<213> ORGANISM: artificial
<220> FEATURE:
<223> OTHER INFORMATION: CaaX-polylysine motif of Kras

<400> SEQUENCE: 17
aagaagaaga agaagaagaa gagcaagacc aagtgcgtga tcatg          45
```